United States Patent
McKeen et al.

(10) Patent No.: US 9,435,818 B2
(45) Date of Patent: Sep. 6, 2016

(54) SAMPLE TRANSPORT SYSTEMS AND METHODS

(75) Inventors: Brian J. McKeen, Bow, NH (US); Eric D. Yeaton, Epsom, NH (US); James L. Dowling, Milford, NH (US)

(73) Assignee: Roche Diagnostics Hematology, Inc., Westborough, MA (US)

( * ) Notice: Subject to any disclaimer, the term of this patent is extended or adjusted under 35 U.S.C. 154(b) by 236 days.

(21) Appl. No.: 13/548,844

(22) Filed: Jul. 13, 2012

(65) Prior Publication Data

US 2013/0020175 A1 Jan. 24, 2013

Related U.S. Application Data

(60) Provisional application No. 61/510,594, filed on Jul. 22, 2011.

(51) Int. Cl.
 *G01N 35/04* (2006.01)
 *G01N 35/02* (2006.01)
 (Continued)

(52) U.S. Cl.
 CPC ............... *G01N 35/04* (2013.01); *G01N 1/31* (2013.01); *G01N 35/00029* (2013.01);
 (Continued)

(58) Field of Classification Search
 CPC .............. G01N 1/31; G01N 35/0099; G01N 2035/0415; G01N 35/02; G01N 35/10; G01N 35/04
 USPC ................... 198/468.6, 346.1, 346.2; 422/63
 See application file for complete search history.

(56) References Cited

U.S. PATENT DOCUMENTS 3,517,709 A * 6/1970 Westesson ........... G01N 33/025
 141/100
4,269,803 A * 5/1981 Jessop .............. G01N 35/00029
 422/561
(Continued)

FOREIGN PATENT DOCUMENTS

CN 1 223 721 7/1999
CN 1 334 453 2/2002
(Continued)

OTHER PUBLICATIONS

International Preliminary Report on Patentability in International Application No. PCT/US2012/046726, mailed on Feb. 6, 2014, 8 pgs.

(Continued)

*Primary Examiner* — Thomas Randazzo
(74) *Attorney, Agent, or Firm* — Fish & Richardson P.C.

(57) ABSTRACT

Sample transport systems are described that move a sample carrier from one station to a next station in a sample processing systems. The systems include: a translating member; two or more sample carrier retaining devices attached to the translating member, wherein each of the two or more sample carrier retaining devices can include a retainer portion to temporarily retain one or more sample carriers; and a movement mechanism to move the translating member and the attached sample carrier retaining devices between a first position and a second position; wherein the sample carrier retaining devices are controlled and moved simultaneously to retain a sample carrier when the translating member reaches the first position and to release a sample carrier when the translating member reaches the second position to successively advance sample carriers in the sample processing systems.

25 Claims, 18 Drawing Sheets

(51) Int. Cl.
*G01N 1/31* (2006.01)
*G01N 35/00* (2006.01)

(52) U.S. Cl.
CPC ......... *G01N 35/0099* (2013.01); *G01N 35/02* (2013.01); *G01N 2035/00039* (2013.01); *G01N 2035/041* (2013.01)

(56) References Cited

U.S. PATENT DOCUMENTS

| | | | | |
|---|---|---|---|---|
| 4,710,352 | A * | 12/1987 | Slater | G01N 35/00029 198/465.1 |
| 4,909,992 | A | 3/1990 | Bjorkman | |
| 4,938,334 | A * | 7/1990 | McGinn | B23Q 1/4828 198/346.1 |
| 5,203,445 | A * | 4/1993 | Shiraiwa | H01L 21/67781 198/346.1 |
| 5,215,377 | A * | 6/1993 | Sugano | G01N 5/04 374/14 |
| 5,370,215 | A * | 12/1994 | Markin | B65G 37/02 198/346.1 |
| 5,595,707 | A * | 1/1997 | Copeland | B01F 5/0057 422/63 |
| 6,110,425 | A * | 8/2000 | Gao | G01N 1/2813 422/63 |
| 6,375,898 | B1 * | 4/2002 | Ulrich | G01N 35/00732 422/62 |
| 6,739,448 | B1 | 5/2004 | Bevirt et al. | |
| 7,303,729 | B2 * | 12/2007 | Plank | G01N 1/312 422/536 |
| 7,556,770 | B2 * | 7/2009 | Justin | G01N 21/13 422/63 |
| 8,486,714 | B2 * | 7/2013 | Favuzzi | G01N 1/30 422/50 |
| 8,492,155 | B2 * | 7/2013 | Bunce | G01N 35/028 422/63 |
| 8,741,655 | B2 * | 6/2014 | Justin | G01N 21/13 422/63 |
| 2003/0049170 | A1 | 3/2003 | Tamura et al. | |
| 2004/0072225 | A1 | 4/2004 | Rollins et al. | |
| 2004/0096362 | A1 * | 5/2004 | Barry | B25J 18/04 422/65 |
| 2005/0135918 | A1 | 6/2005 | Tominaga et al. | |
| 2006/0088940 | A1 * | 4/2006 | Feingold | G01N 1/31 436/47 |
| 2008/0014119 | A1 * | 1/2008 | Metzner | G01N 1/312 422/65 |
| 2008/0020467 | A1 * | 1/2008 | Barnes | G01N 35/0092 436/2 |
| 2009/0232704 | A1 * | 9/2009 | Dohmae | G01N 35/0092 422/63 |
| 2012/0144785 | A1 * | 6/2012 | Vaccari | B65G 25/02 53/510 |
| 2012/0149059 | A1 * | 6/2012 | Shah | G01N 1/312 435/40.52 |
| 2012/0290127 | A1 * | 11/2012 | Neef | G01N 35/00029 700/230 |
| 2012/0310401 | A1 * | 12/2012 | Shah | G01N 1/312 700/103 |
| 2013/0035242 | A1 * | 2/2013 | Abenaim | G01N 35/02 506/2 |

FOREIGN PATENT DOCUMENTS

| | | |
|---|---|---|
| CN | 1 512 184 | 7/2004 |
| WO | WO 95/20176 | 7/1995 |

OTHER PUBLICATIONS

Examination Report in Australian Patent Application No. 2012287300, mailed on Feb. 13, 2014, 3 pgs.
International Search Report and Written Opinion dated Sep. 17, 2012 issued in international application No. PCT/US2012/046726, 12 pgs.
English Translation of the First Office Action for corresponding Chinese Application No. 201280046535.1, issued on Apr. 29, 2015, 25 pages.
English Translation of Search Report, for corresponding Chinese Application No. 201280046535.1, issued on Apr. 29, 2015, 6 pages.
English Translation of the Second Office Action for corresponding Chinese Application No. 201280046535.1, issued Feb. 15, 2016, 33 pages.
English Translation of the Japanese Office Action for corresponding Application No. 2014-5201672, issued on Mar. 29, 2016, 7 pages.

* cited by examiner

SAMPLE TRANSPORT SYSTEMS AND METHODS

CROSS-REFERENCE TO RELATED APPLICATIONS

This application claims priority under 35 U.S.C. §119(e) to U.S. Provisional Patent Application No. 61/510,594, filed on Jul. 22, 2011, the entire contents of which are incorporated by reference herein.

TECHNICAL FIELD

This disclosure relates to carriers containing or supporting samples, such as samples of fluids, e.g., biological fluids, and more particularly to methods and systems for transporting carriers such as glass or plastic slides, that carry samples.

BACKGROUND

Systems, such as manufacturing systems or systems for analyzing samples, e.g., fluid samples, tissue samples, food samples, chemical samples, environmental samples, etc., can have multiple processing stations. To permit automatic or semi-automatic operation of such systems (e.g., to minimize human interaction), electromechanical systems can be implemented to move samples throughout the processing stations.

SUMMARY

Systems, such as manufacturing or testing systems, e.g., blood analysis systems, having multiple stations, e.g., processing, monitoring, or analysis stations, can be simplified by creating a transport mechanism that can simultaneously move samples, e.g., fluid samples, tissue samples, food samples, chemical samples, environmental samples, etc., from one processing station to a next processing station. In some aspects of the disclosure, the transport mechanism can operate via a single motion input, such as a leadscrew connected to a motor or a slide mechanism, which translates between a first position and a second position to provide samples to successive processing stations.

In one implementation, the present disclosure relates to sample transport systems that move a sample carrier from one station to a next station in a sample processing system, and the sample transport systems include: a translating member; two or more sample carrier retaining devices attached to the translating member at a fixed, equal spacing between adjacent sample carrier retaining devices, where each of the two or more sample carrier retaining devices can include a retainer portion to temporarily retain one or more sample carriers; and a movement mechanism connected to the translating member to move the translating member and the attached sample carrier retaining devices back and forth between a first position and a second position; where the sample carrier retaining devices are all moved and controlled simultaneously to enable each respective retainer portion to contact and retain a sample carrier when the translating member reaches the first position and to release a sample carrier when the translating member reaches the second position, such that as the translating member moves back and forth between the first position and the second position, sample carriers are advanced successively from one station to a next station in the sample processing system.

Implementations of the sample transport systems can include any one or more of the following features, individually or in combination. The sample carrier can include one or more of a metal, glass, ceramic, or plastic (e.g., a glass microscope slide). At least one of the sample carrier retaining devices can be moved and controlled by the translating member to transport the sample carrier to a specific station in a proper orientation to retain or release the sample carrier at the specific station, where the proper orientation of the sample carrier can be achieved by rotating at least the retainer portion as the sample carrier retaining device moves towards the specific station, and where the proper orientation of the sample carrier can be achieved by rotating at least the sample retainer portion horizontally to a specific angle from 90 to 180 degrees. The retainer portions can include a vacuum cup, an adhesive material, an electromagnet, or a mechanical device configured to hold a sample carrier.

The movement mechanism can include an electric motor and leadscrew or a pneumatic or magnetic linear actuator. The movement mechanism can move all sample carrier retaining devices vertically and horizontally between a first position and a second position and rotates a subset of the sample carrier devices to a proper orientation at the second position.

The sample transport systems can further include a device to lift and lower the translating member to simultaneously lift and lower all attached sample carrier retaining devices, wherein the device to lift and lower the translating member can include a member that travels along a profiled aperture within a horizontal beam. The sample processing systems can include six stations and the sample transport systems can include five sample carrier retaining devices, wherein the sample processing systems can include a slide magazine to provide empty sample carriers, a sample applicator configured to apply an aliquot of a sample to sample carriers, a sample stainer configured to apply one or more stains to samples on sample carriers, a low magnification imaging station to image at least a portion of samples on sample carriers, a high magnification imaging station to image a portion of samples on sample carriers, and a slide output station, and wherein the sample transport system comprises five sample carrier retaining devices that successively advance sample carriers from one station to a next station in the sample processing system.

In another implementation, the present disclosure relates to methods of transporting a sample on a sample carrier from one station to a next station in a sample processing system. The methods include obtaining a translating member that moves back and forth between a first position and a second position, where two or more sample carrier retaining devices are attached to the translating member at a fixed, equal spacing between adjacent sample carrier retaining devices; moving the translating member into the first position such that the sample carrier retaining devices are all moved and controlled simultaneously to enable each to contact and retain a sample carrier at a station; and moving the translating member into the second position such that the sample carrier retaining devices are all moved and controlled simultaneously to enable each to release a sample carrier at a station; where sample carriers are advanced successively from one station to a next station in the sample processing system.

Implementations of the methods can include any one or more of the following features individually or in combination. The sample carrier can be provided to the next successive station in a proper orientation, where the proper orientation for the next successive station can be achieved by rotating the sample carrier retaining device, and the proper orientation for the next successive station can be achieved by rotating the sample carrier retaining device. Moving a translating member between a first position and a second position can include operating an electric motor and leadscrew, or a pneumatic or magnetic linear actuator. Moving a translating member can include raising the translating member to remove a sample carrier from a station and lowering the translating member to place a sample carrier onto the next successive station. The sample can include a body fluid (e.g., blood). The sample carrier retaining devices can each include a retainer portion including a vacuum cup, an adhesive material, an electromagnet, or a mechanical device configured to hold a sample carrier.

The methods of transporting a sample can further include moving a sample carrier from a last successive station to a sample output mechanism.

Further, implementations can include any of the other features disclosed herein, including features disclosed with respect to other implementations, in any combination as appropriate, unless specifically excluded.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, and from the claims.

DESCRIPTION OF DRAWINGS

Like reference symbols in the various drawings indicate like elements.

DETAILED DESCRIPTION

Figure 1:
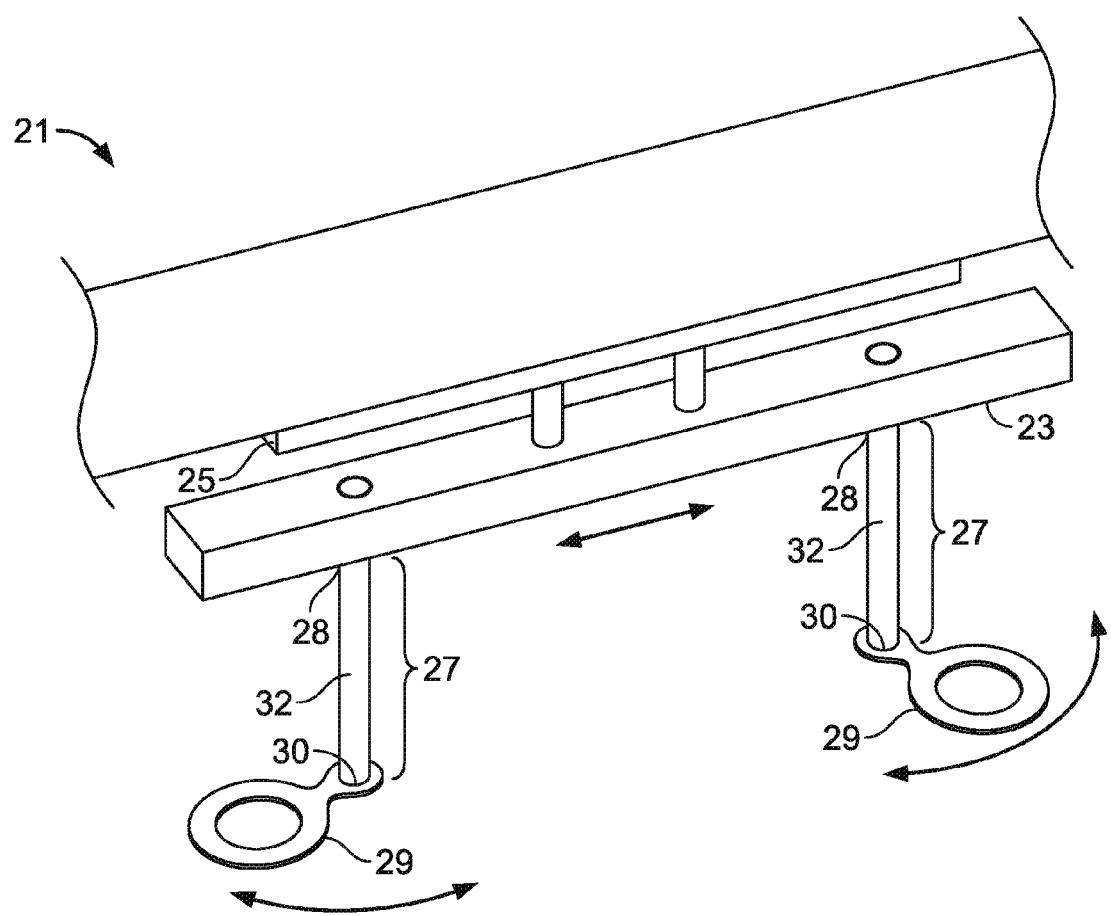
FIG. 1 is a perspective view of a sample carrier transport system for transporting sample carriers between first and second processing stations.

For automated testing of samples, e.g., samples of tissues or fluids such as biological fluids (e.g., blood), the new systems and methods disclosed herein can be used to transport sample carriers, such as slides, that contain or support the sample throughout various stations or modules of an automated testing and/or monitoring system or apparatus.
Sample Carrier Transport Systems FIG. 1 shows a sample carrier transport system 21 used to provide a sample to one or more stations, e.g., analysis, monitoring, or processing stations, of a sample analysis and/or processing system. The sample carrier transport system 21 includes a translating member 23, a movement mechanism 25, and a plurality of carrier retaining devices 27 to transport a plurality of sample carriers 29.

The translating member 23 is a component or device that can move two or more sample carriers 29 to and from two or more stations simultaneously. The translating member 23 can be in the form of a translating beam from which samples carried by sample carriers 29 can be suspended using the carrier retaining devices 27. Alternatively or additionally, in other implementations, sample carriers 29 can rest on top of a translating member 23 in the form of an articulating track or conveyor belt which moves sample carriers. The sample carrier retaining devices 27 are fixed to the translating member 23 at an equal spacing between adjacent retaining devices, so that all of the retaining devices move simultaneously when the translating member 23 moves.

The movement mechanism 25 moves the translating member 23. The movement mechanism 25 can be configured to move the translating member 23 through multiple positions, such as, a first position and a second position (e.g., a pick-up position and a drop-off position), which can correspond with the quantity and location of stations (e.g., processing stations). The movement mechanism 25 can be implemented in many forms, such as an electric motor connected to a leadscrew mechanism, a conveyor belt, a chain drive, a linear actuator (e.g., a pneumatic linear actuator or a magnetic linear actuator), a pneumatic translating device, or a magnetic track, among other possible mechanisms. Pneumatic or hydraulic linear actuators can operate using a piston that can move along the inside of a cylinder. Air or liquid pressure can be used to move the piston along the cylinder by increasing the pressure on one side of the piston and decreasing the pressure on the other side of the piston. Magnetic linear actuators operate in a manner similar to an electric motor. However, instead of generating and using electromagnetic forces to turn a rotor, the magnetic linear actuator can use electromagnetic forces to translate a device along a track. As further described below, certain embodiments can advantageously use a single movement mechanism to impart pure vertical and horizontal motion (i.e., non-parabolic motion), as well as rotational movement, to multiple carrier retaining devices.

To transport the sample carriers 29 to each of two or more processing stations, the sample carrier transport system 21 has two or more carrier retaining devices 27 that are attached to the translating member 23 such that when the translating member 23 moves, all of the carrier retaining devices 27 move simultaneously. Typically, the number of carrier retaining devices 27 used in the sample carrier transport system 21 is based on the number of stations in a given sample processing system, and to operate properly, there is typically one carrier retaining device 27 that shuttles back and forth between two adjacent stations. For example, if the analysis system has a number "n" of stations (i.e., stations that process a sample, or stations that provide an input of samples on carriers or stations that dispose of samples), the sample carrier transport system 21 will generally have "n−1" carrier retaining devices 27. Thus, if there are three stations, there can be two carrier retaining devices.

In some sample processing systems there are six (i.e., n=6) stations, for example, including a slide magazine from which empty slides (sample carriers) are obtained, a sample applicator, which applies an aliquot of sample to each slide, a sample stainer, a low magnification imaging station, a high magnification imaging station, and a slide output station, which determines whether a given slide is to be saved for further review, or directed to waste. In such a system, there can be five (i.e., n−1) sample carrier retaining devices.

The methods of transport and the sequence of motion of the sample carrier transport system 21 are discussed in greater detail below.

The carrier retaining devices 27 themselves can include several components, including attachment devices 28 to attach the carrier retaining devices 27 to the translating member 23, retainer portions 30 to temporarily attach to sample carriers 29, and elongated members 32 to position the retaining portions 30 at a distance from the attachment devices 28, and thus from the translating member 23. Carrier retaining devices 27 are generally positioned equidistant from each adjacent retaining device on the translating member 23. The distance between the retaining devices generally corresponds to the distance between stations in the system, such that the sample carrier transport system 21 can properly transport sample carriers 29 to and from each of the stations uniformly and simultaneously.

The retaining portions 30 of the carrier retaining devices 27 can be implemented in various forms to firmly, but releasably, attach to the sample carriers. The retaining portions can be in the form of vacuum cups (e.g., pneumatic vacuum cups), adhesive materials, electromagnets, and mechanical grabbing devices, such as mechanical fingers or mechanical locking tabs. The attachment device 28, located at the other end of the elongated member 32 from the retaining portion, can include a rigid or flexible portion (e.g., springs or flexible members) to allow for smoothly picking up and dropping off sample carriers 29 and to avoid inadvertent breaking of the sample carriers 29.

In some implementations, in addition to attaching to sample carriers 29, the carrier retaining devices 27 can have rotation mechanisms to rotate the sample carriers 29 such that while the carriers are moving to the next processing station, they are also rotating to a proper orientation and position for being deposited at that particular processing station. The rotation mechanisms can be designed such that they rotate the entire carrier retaining devices 27, or alternatively the rotation mechanisms can rotate only a part of the carrier retaining device (e.g., the retaining portions 30), and thus the sample carriers 29.

Although the carrier retaining devices 27 have been described as being attached to move uniformly with a translating member 23, in other implementations, each carrier retaining device 27 can be associated with a separate translating device to move them individually.

The sample carriers 29 are used to carry (e.g., contain or support) samples (e.g., specimens prepared from fluid samples, such as blood, and deposited on a glass microscope slide) to each of the processing stations. Sample carriers 29 can be in many forms, such as small cups or trays made of metal, glass, plastics, or similar materials (e.g., glass slides). The type of sample carrier 29 used can depend on the type of sample being transported and the requirements of the system in which the sample carrier transport system 21 will be used. For example, if the sample carrier transport system 21 transports tissue samples, simple flat slides may be used, whereas if the sample carrier transport system 21 transports large amounts of liquid, a cup-type carrier may be more appropriate.

Generally, the sample carriers 29 and the carrier retaining devices 27 can be designed specifically to integrate with each other. The choice and combination of sample carrier 29 and carrier retaining device 27 can also be influenced by the type of sample to be transported. For example, if liquids are transported in metal cup-type sample carriers 29 then magnetic carrier retaining devices 27 can be used. Alternatively, if a sample is applied to a glass slide, vacuum cups may be used as carrier retaining devices 27.

Systems for Analyzing Samples

Figure 2:
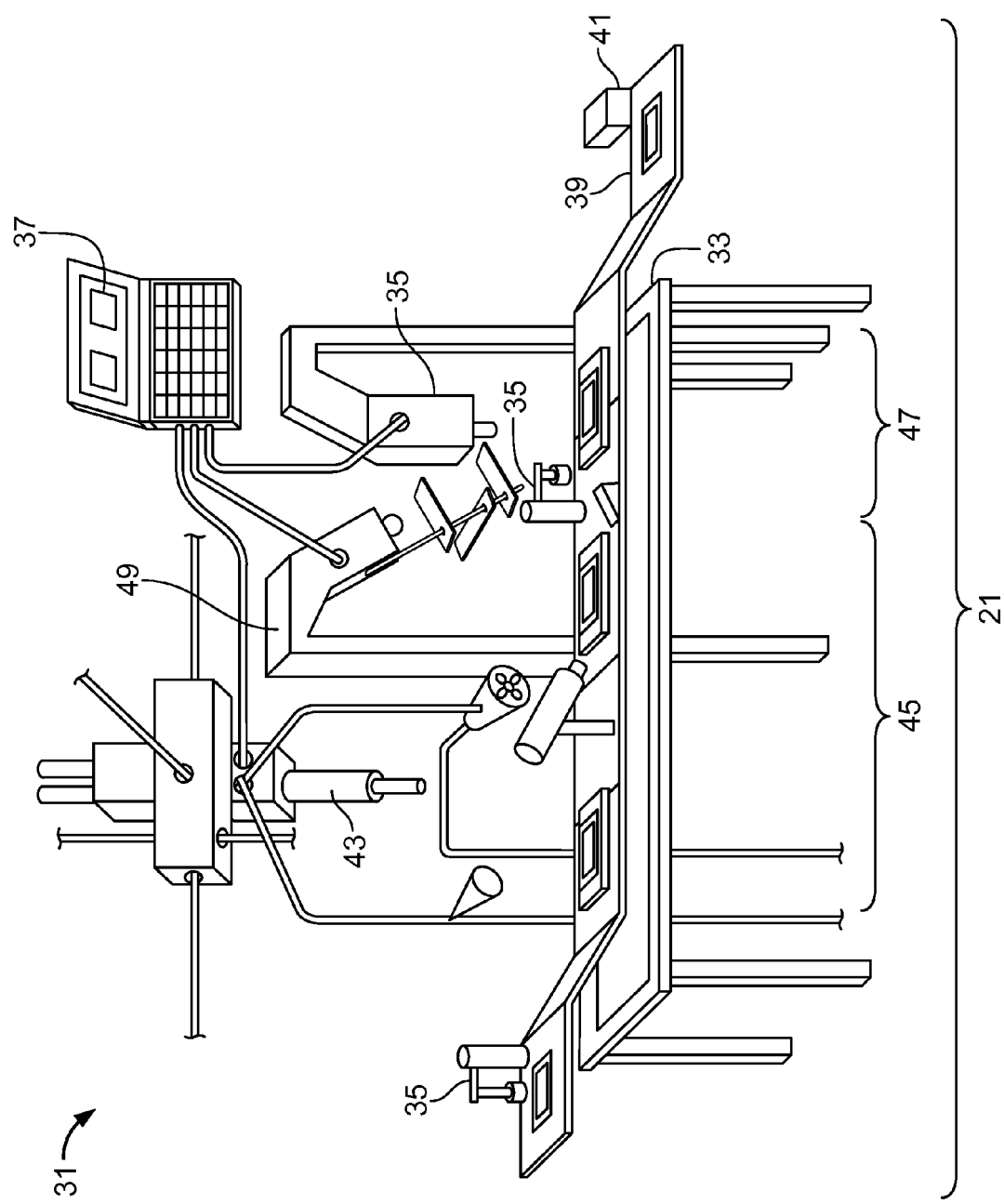
FIG. 2 is a perspective view of an analysis system for analyzing samples such as fluids, e.g., body fluids.

FIG. 2 shows an analysis system 31 for analyzing samples such as body fluids. As discussed in U.S. Patent Application No. US 2009/0269799, U.S. Published Patent Application No. US 2011/0070606, and U.S. patent application Ser. No. 12/943,687, the entire contents of each of which are incorporated by reference herein, systems for analyzing fluid samples can include subsystems and components to inspect body fluids such as blood. Components can include a chassis 33, a sample carrier transport system 21, one or more processing stations 35, a control unit 37, a slide output station 39, and a sample carrier labeler 41.

The chassis 33 supports all of the components of the system. In some implementations, the chassis is in the form of a platform or table onto which system components are affixed on a housing in which the system components are secured.

The analysis system 31 can include one or more (e.g., 1, 2, 3, 4, 5, 6, 7, 8, 9, 10, or more) processing and analysis stations 35 to perform various processes. When analyzing a biological fluid, processing stations 35 can include a sample applicator 43, a sample preparation (e.g., staining) station 45, and/or one or more imaging stations 47. Additionally, the analysis system 31 may contain stations that do not have processing components to possibly reserve the location for future needs or uses. Processing stations 35 can be positioned in a straight direction with respect to one another, or alternatively the processing stations 35 can be positioned in an arc or other shapes based on system and/or space requirements.

As discussed above, to transport the sample carriers 29 to the processing stations 35, the sample carrier transport system 21 can have a translating member 23 having two or more carrier retaining devices 27 attached.

Although the analysis system 31 shown in FIG. 2 has one sample carrier transport system 21, in some implementations, the analysis system 31 can include two or more sample carrier transport systems 21. For example an analysis system 21 can include two or more sample carrier transport systems 21 working in parallel.

Systems and methods for analyzing body fluids are disclosed, for example, in U.S. Patent Application Publication Nos. 2011/0070606 and 2012/0149050, and in PCT Patent Application Publication No. WO 2010/126903, the entire contents of each of which are incorporated herein by reference. The sample applicator 43 can be a device used to deliver a sample to a sample carrier 29. In some implementations, the analysis system 31 analyzes body fluids, so the sample applicator 43 is configured to dispense a metered amount of fluid onto each of the sample carriers 29. Such sample applicators can be powered pneumatically using suction to withdraw a fluid from a reservoir and then to dispense the fluid into or onto the sample carrier 29. Depending upon the type of samples analyzed by the analysis system 31, other types of sample applicators 43 are possible. For example, if tissue samples are analyzed, the sample applicator can include a type of mechanical device to pick up the tissue, such as tweezers or forceps.

Some sample types such as body fluids (e.g., blood, bone marrow, urine, semen, bile, breast milk, cerebrospinal fluid, gastric fluid, mucus, peritoneal fluid, sweat, tears, and/or saliva) can be analyzed with a stain applied to permit certain types of visual inspection. In such analysis, the sample preparation station 45 can apply one or more fixatives, stains, and/or rinse solutions to the sample carried by the sample carrier 29.

To inspect or analyze the sample using the imaging station 47, a light source 49 is generally included in the system to illuminate the sample. Depending on the type of analysis to be conducted, the light source 49 can include various types of visible light sources (e.g., light emitting diodes, incandescent lights, fluorescent lights, and/or lasers) or non-visible light source (e.g., ultraviolet light and infrared light sources). The positioning of the light source 49 relative to the sample can depend on the type of analysis conducted, as well as on the type of sample carriers 29 used. In some implementations, where samples are carried on glass slides, an LED light source is positioned below the glass slides to illuminate the sample.

The imaging station 47 is electrically connected to the control unit 37 and can be used to collect data from samples (e.g., can take an image of the sample to perform algorithms or analyses using the image). In some implementations, the imaging station 47 can use the image to perform analyses such as counting blood cells in a sample or to detect specific cells in the blood. As discussed above, in some implementations, the light source 49 can provide different forms of light so the imaging station 47 can therefore include other types of detectors such as infrared light detectors or laser detectors used to measure certain properties (e.g., dimensions) of the sample.

Once the analysis system 31 has processed the sample at all of the processing stations 35, the slide output station 39 either discards the sample or retains the sample for additional processing or future evaluation.

In such cases where it is desired to retain the sample and/or sample carrier 29 for additional processing or evaluation, a sample carrier labeler 41 (e.g., a printer device) can be used to provide sample information to the sample and/or to the sample carrier 29. For analysis systems 31 that analyze a patient's body fluids, the patient's information can be printed onto the sample carrier.

The control unit 37 can be electrically connected to the various components of the system to control the operations of the components such as controlling the sample carrier transport system 21, the light source 49, the imaging system 47, and the sample carrier labeler 41.

Transporting Samples Through an Analysis System

Figure 3:
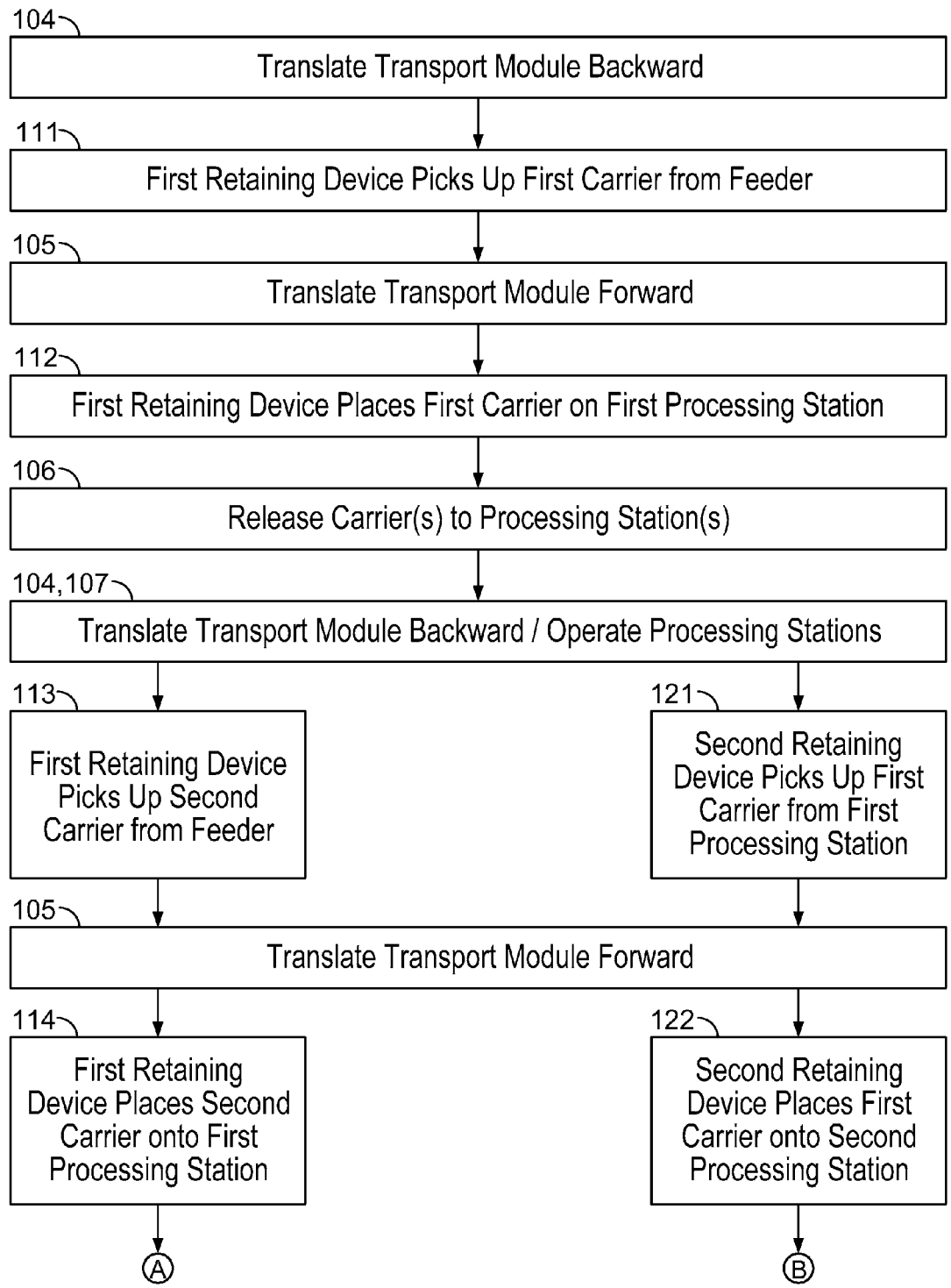
FIG. 3 is a flow chart of a sample carrier transport system.
Figure 3:
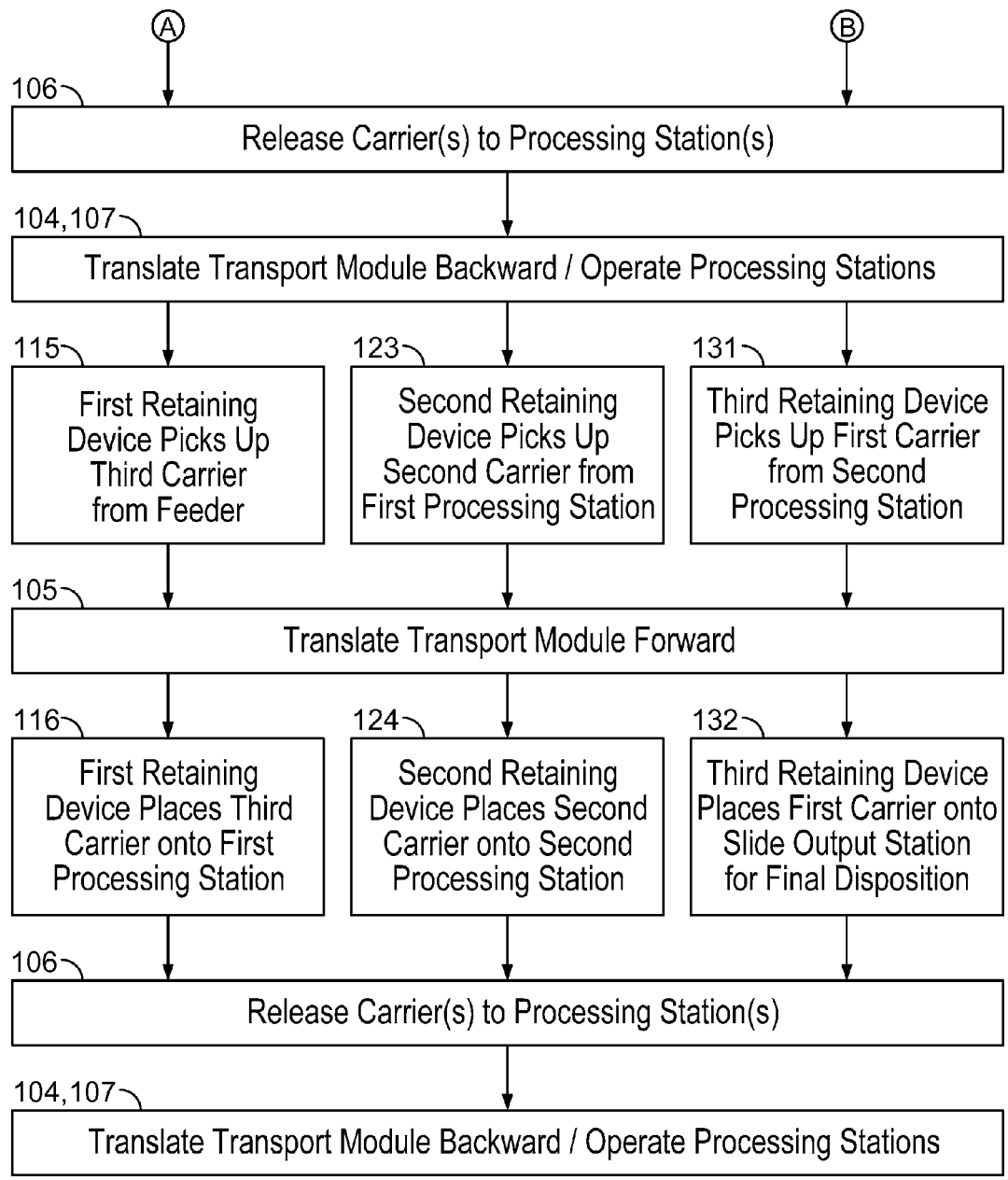

FIG. 3 shows a flow chart that includes a series of steps for transporting one or more sample carriers through an automated or semi-automated analysis system for analyzing samples (e.g., samples of fluids, such as biological fluids). The analysis system transports sample carriers to carry samples through the system, one or more processing stations to perform various processes (e.g., applying a sample to a carrier or taking an image of the sample), and a plurality of carrier retaining devices.

In this example, the system includes sample carriers, a sample feeder, two processing stations, a sample output station, and three carrier retaining devices that are configured to move uniformly (e.g., all of the carrier retaining devices are attached to a translating member). However, in other implementations, more processing stations and carrier retaining devices can be used based on the system.

A plurality of sample carriers is provided in a carrier magazine. The carrier magazine is a device for containing and/or transporting the sample carriers. As discussed above, the sample carriers can be cups, test tubes, or flat plates (e.g., glass microscope slides). The carrier magazine is configured so that a first sample carrier can be removed from the carrier magazine with a feeder and a next sample carrier is then in a position where it can be removed, followed by a next carrier.

Using the feeder, carriers are removed from the carrier magazine and placed in a position such that a carrier retaining device connected to the translating member can pick up the sample carrier. The feeder can remove the carriers from the magazine using various methods such as magnets, mechanical "fingers," vacuum, springs, gravity, and/or hydraulics, depending on the type of carrier used and the configuration of the analysis system. Upon removing the sample carrier from the carrier magazine, the feeder can rotate and/or translate to provide the sample carrier in the proper position and orientation for contact with a first carrier retaining device.

In some implementations, more than one sample carrier can be removed at a time. For example, two carriers could be removed and provided to two sample carrier transport systems operating in parallel. Alternatively two sample carriers could be removed to proceed successively down one sample carrier transport system.

As shown in FIG. 3, to begin processing a first sample carrier, the translating member and carrier retaining devices translate backward (step 104) and a first carrier retaining device picks up the first sample carrier from the feeder (step 111). With regards to the motion of the translating member, forward indicates the direction of travel of the sample carriers during processing (e.g., away from the carrier magazine) and backward indicates the direction opposite the direction of travel of the sample carriers during processing (e.g., towards the carrier magazine). When the first sample carrier is picked up by the first carrier retaining device (step 111), the translating member translates forward (step 105) such that the first carrier retaining device provides the first sample carrier to a first processing station (step 112). Once the first sample carrier is placed onto the first processing station (step 112), the first carrier retaining device releases the first sample carrier (step 106), and the translating member, with carrier retaining devices attached, translates backward (step 104). While the translating member moves backward (step 104), the sample is processed at the first processing station (step 107). As processing occurs, the feeder removes a second sample carrier from the carrier magazine and moves it into position for removal.

At the next step, when the translating member translates backward (step 104), the first carrier retaining device approaches the feeder to pick up the second sample carrier (step 113). Since the carrier retaining devices are affixed to the translating member, as the first carrier retaining device approaches the second sample carrier (step 113), a second carrier retaining device approaches the first sample carrier that is positioned on the first processing station (step 121). The translating member continues to move backward until the carrier retaining devices contact and retain the sample carriers (i.e., the first carrier retaining device picks up the second sample carrier from the feeder (step 113) and, e.g., simultaneously the second carrier retaining device picks up the first sample carrier from the first processing station (step 121).

With both the first sample carrier and the second sample carrier retained, the translating member moves forward (step 105) to advance the sample carriers to the next successive station. Therefore the first sample carrier is provided to a second processing station (step 122) and the second sample carrier is provided to the first processing station (step 114). The sample carriers are placed into position onto each of the processing stations and are released from the carrier retaining devices for processing at the processing stations (step 106). While the samples are processed (step 107), the feeder removes a third sample carrier from the carrier magazine and moves it into position for removal.

While processing occurs, the translating member and the carrier retaining devices translate backward (step 104) again such that the first carrier retaining device approaches the feeder containing the third sample carrier positioned for removal (step 115), the second carrier retaining device approaches the first processing station where the second sample carrier is positioned (step 123), and the third carrier retaining device approaches the second processing station where the first sample carrier is positioned (step 131). Once the carrier retaining devices come into contact with each of the sample carriers, they simultaneously pick up all three sample carriers and the translating member with the carrier retaining devices and the attached sample carriers translate forward to move the sample carriers to the next station (step 105). The first sample carrier has been processed at both the first and second processing stations, so it is moved to a slide output station for final disposition (step 132) (e.g., to be discarded or retained). The second sample carrier is moved to the second processing station (step 124), and the third sample carrier is moved to the first processing station (step 116). This process moves each of the sample carriers to all of the processing stations of the analysis system with each carrier in the proper orientation for a given station, via motion of the translating member between two positions, the pick-up position and the drop-off position. In addition, this process can repeat continuously until all samples presented to the analysis system or all sample carriers within the carrier magazine have been processed through all of the processing stations of the analysis system.

Although this analysis system has been described as having two processing stations, this process can be performed with more than two processing stations. For example, in other implementations, more than two (e.g., three, four, five, six, seven, eight, nine, ten, or more) processing stations can be included in the analysis system. In such implementations, the transport method including translating a translating member with carrier retaining devices between a pick-up position and a drop-off position can be performed by providing additional carrier retaining devices connected to the translating member.

Fluid Sample Transport Systems

Figure 4A:
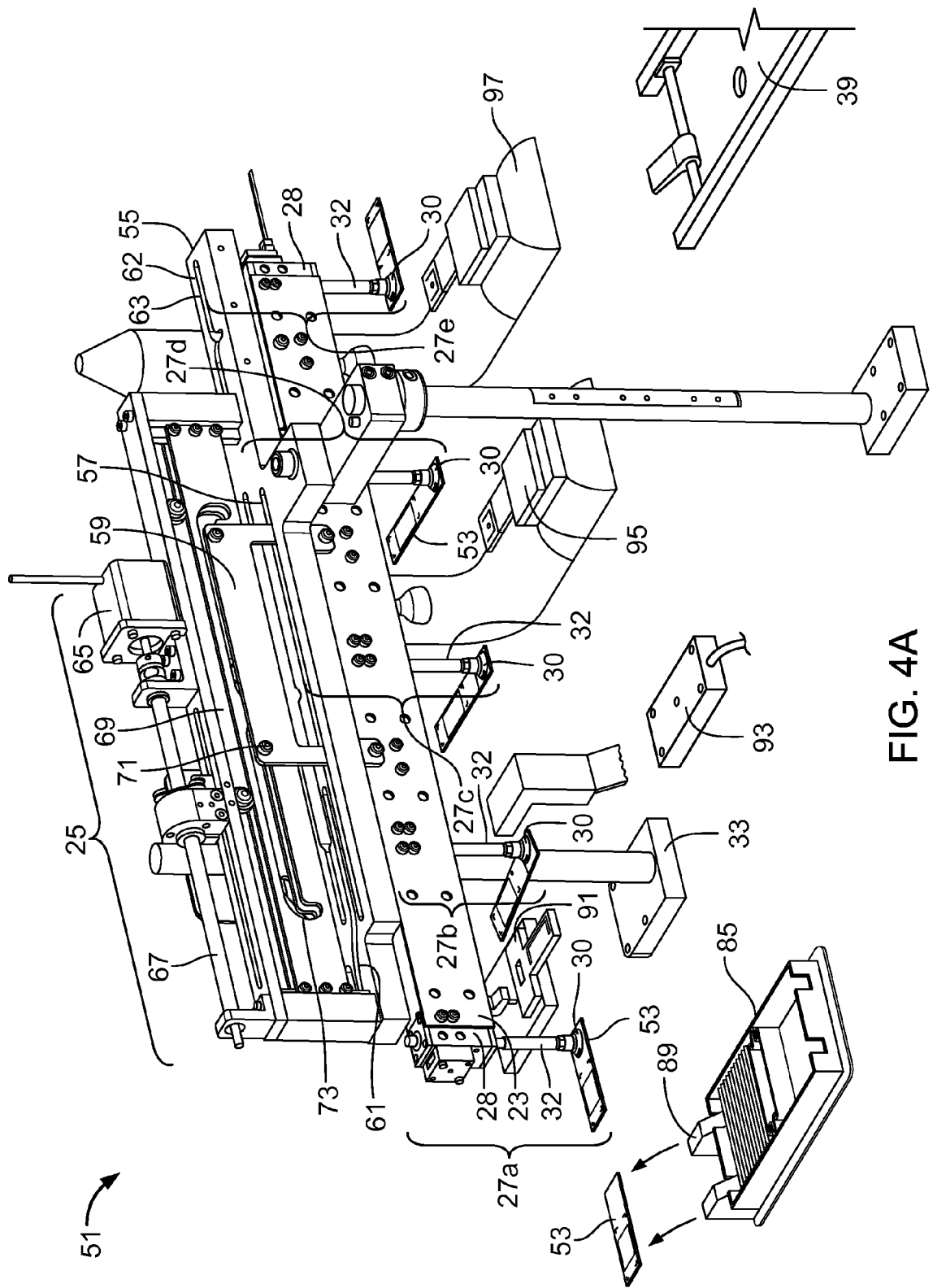
FIG. 4A is a perspective view of a slide transport system.

FIG. 4A shows an example of a biological fluid sample carrier transport system used in a biological fluid analysis system, in the form of a slide transport module 51. The slide transport module 51 carries slides 53 (e.g., glass microscope slides) to and from multiple stations of the analysis system.

Components and stations of the analysis system can include a slide magazine 85, a slide feeder 89, a sample print station 91, a sample preparation station 93, a low magnification imaging station 95, a high magnification imaging station 97 and a slide output station 39. The slide magazine 85 is used to contain and provide a plurality of sample slides 53 (e.g., glass microscope slides) to the sample transport system 51. The slide feeder 89 is an articulating device that removes slides 53 from the slide 85 magazine and provides them to the slide transport module 51 for use in the analysis system. The sample preparation station 93 applies a sample (e.g., a fluid sample such as, for example, blood) to the glass slide 53 for inspection. The sample preparation station 93 can be used to apply one or more fixative, staining, and/or rinse solutions to a fluid sample to preserve and prepare the sample for evaluation at one or more imaging stations. After the sample has been prepared (e.g., applied to a slide and treated with one or more fixative, stain, and/or rinse solutions), the low magnification imaging station 95 can capture a low magnification image of the sample for analysis. For further inspection, the high magnification imaging station 97 is provided to obtain one or more higher magnification images of the sample for processing. After the sample has been to each of the stations for analysis, the slide 53 is provided to the slide output station 39 for disposition. Typically the slide 53 can either be discarded or it can be retained by the system for additional consideration and/or storage. The components and stations of the analysis system will be discussed in greater detail below with regard to the operation of the system.

The slide transport module 51 can include a base beam 55, a translating member 23, a plurality of carrier retaining devices 27 (e.g., 27*a-e*), and a movement mechanism 25.

The base beam 55 is rigidly connected to a chassis 33 of the biological fluid analysis system and provides mounting locations for the movement mechanism 25 and other components. The base beam 55 has multiple grooves 57 through which connecting beams 59 pass to connect to the translating member 23 and multiple slots 61 in which carrier retaining device pins 63 can move.

The movement mechanism 25 is in the form of an electric motor 65 (e.g., one motor to control all motions of the translating member 23), which rotates a leadscrew 67 to move a movement beam 69. The movement beam 69 is connected to the translating member 23 by one or more connecting beams 59. The connecting beams 59 are attached to the movement beam 69 using fasteners 71 (e.g., screw, pins, bolts or similar). The fasteners 71 are designed to travel along one or more lift/lower slots 73, which provide proper lifting and lowering of the connecting beam 59, translating member 23, and carrier retaining devices 27 at pick-up and drop-off positions during translation.

Therefore, as the electric motor 65 rotates the leadscrew 67, it translates the movement beam 69 and connecting beams 59 such that the connecting beams 59, and therefore also the translating member 23 and carrier retaining devices 27 travel, following the path of the lift/lower slot 73. In other implementations, the translating member 23 can have one or more actuator devices (e.g., servos) to provide lifting and lowering capabilities at each station location. As discussed in detail herein, the motion of substantially all of the components of the slide transport module 51 are controlled and operated by the rotation of the electric motor 65 and the single linear force generated by the electric motor 65 and the leadscrew 67. As the leadscrew rotates, the lifting and lowering of the translating member 23 and the plurality of carrier retaining devices 27, as well as the rotation of any carrier retaining devices 27 that rotate during operation, can all be simultaneously driven by a single force input (e.g., the rotation of the electric motor 65).

Figure 4B:
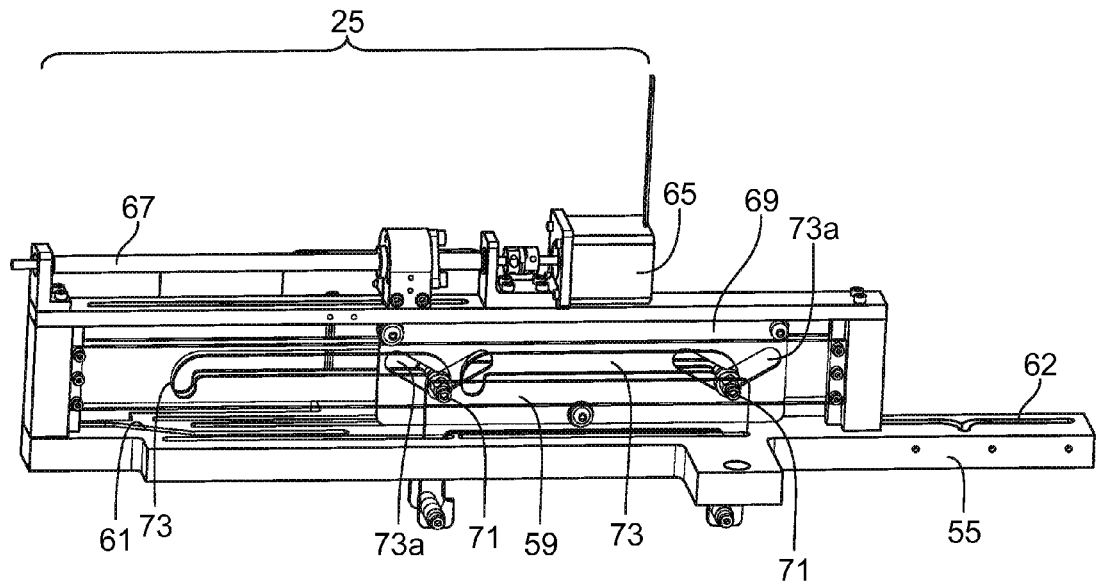
FIGS. 4B-4D are schematics that show sequential vertical and then horizontal movements of connecting beams of the slide transport system of FIG. 4A.
Figure 4C:
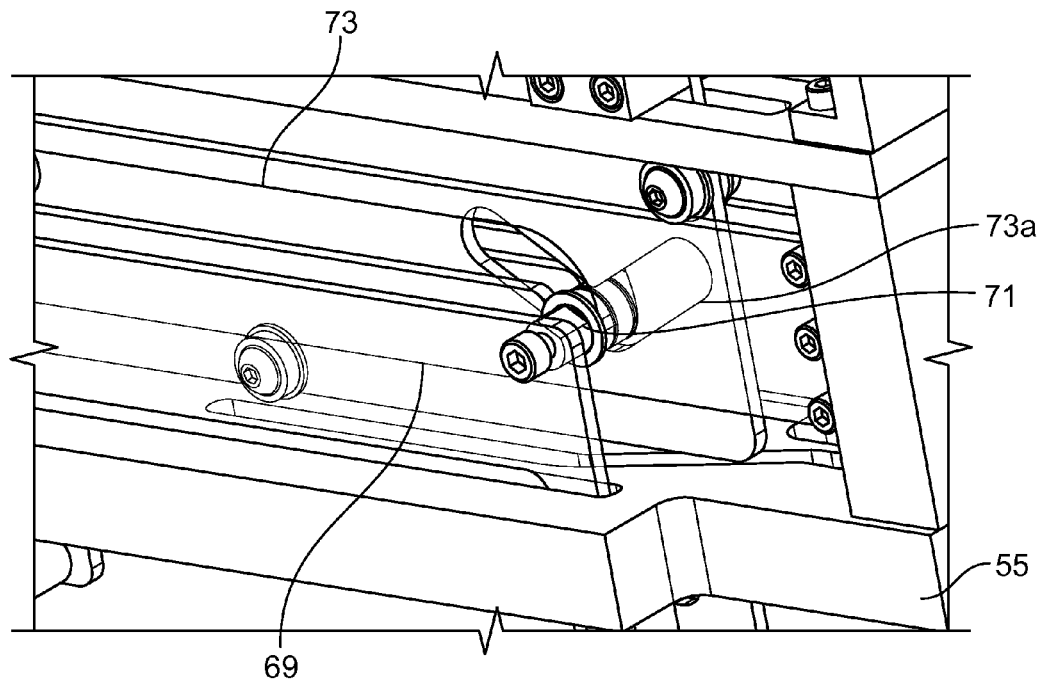
Figure 4D:
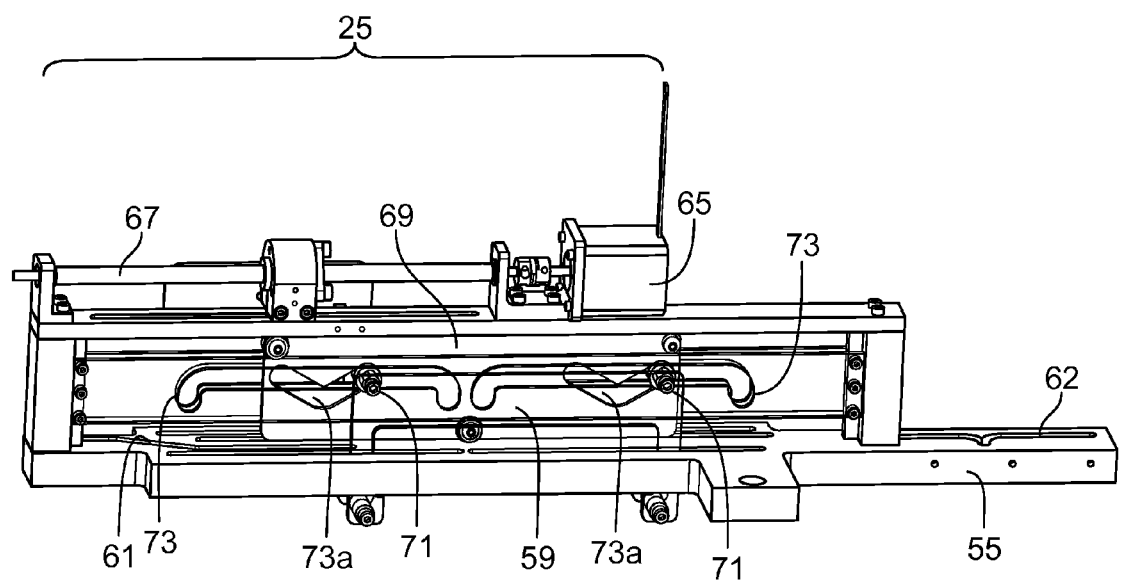

FIGS. 4B-4D show the movement beam 69 and the other components used to lift and translate the connecting beams 59 and translating member 23 during sample transport. As shown, in some implementations, the movement beam 69 can also include one or more slots 73a (e.g., v-shaped slots) along which the fasteners 71 travel. By including a stationary lift/lower slot 73 and a v-shaped slot 73a on the movement beam 69, the translating member 23 (not shown in FIGS. 4B-4D) can have both true vertical and true horizontal motion.

As shown in FIG. 4B, when the movement beam 69 is at a lowered position, to lift and translate the movement beam 69 the movement mechanism 25 applies a single force input (e.g., the electric motor 65 rotates the leadscrew 67) that begins to translate the movement beam 69 (in FIGS. 4B and 4C the movement beam 69 begins to move to the left). As the movement beam 69 begins to move leftward, the inclined surface of the v-shaped slot 73a provides a lifting force to the fastener 71. Since the fasteners are not rigidly connected to the movement beam 69, the fastener 71 is able to slide upward along the v-shaped slot 73a as the movement beam 69 moves leftward, which also causes the fastener 71 to move upward along the lift/lower slot 73. Therefore, although the single force input causes the movement beam 69 to move horizontally, the combination of the lift/lower slot 73 and the v-shaped slot 73a cause the fasteners 71, and thus the connecting beams 59 that are typically connected to the translating member 23, to move purely vertically over a portion of the travel of the movement mechanism 25.

The speed at which the fasteners 71 move upward along the lift/lower slot 73 when the movement beam 69 moves horizontally depends on the incline of the v-shaped slot 73a (e.g., the angle between the two straight segments) as well as the horizontal speed of the movement beam 69. Typically, the steeper the incline, the faster the fasteners will tend to travel up the lift/lower slot 73. However, the shape of the lift/lower slot 73 and the v-shaped slot 73a can be optimized to meet system performance requirements.

As shown in FIG. 4D, once the fasteners 71 are moved upward far enough so that they reach the top of the vertical portions of the lift/lower slot 73, the outward most end of the v-shaped slot 73a provides a horizontal force to provide purely horizontal motion to the fastener 71, and therefore also to the connecting beams 59 and translating member 23.

Although this method of providing both purely vertical motion and purely horizontal motion has been described as moving the fasteners 71 and connecting beams 59 upward and then leftward, the substantially symmetric lift/lower slots 73 and v-shaped slots 73a can also be used to move the fasteners 71 and connecting beams 59 upward and horizontally in the right direction when the fasteners 71 and connecting beams 59 are at their most leftward and lowered position.

Referring back to FIG. 4A, in some implementations, the translating member 23 has five carrier retaining devices 27a, 27b, 27c, 27d, and 27e attached having retaining portions 30 in the form of vacuum cups that are attached to a distal end of elongated members 32 in the form of cylindrical beams. The five carrier retaining devices 27a, 27b, 27c, 27d, and 27e are positioned equidistant from each other and provide the ability to pick up and carry slides 53 during use. The carrier retaining devices are equipped with vacuum capabilities such that when the vacuum cups 30 are depressed onto glass slides 53 and lifted, the slides 53 will remain in contact, lift, and travel towards a next processing station with the carrier retaining devices and vacuum cups 30.

Although some of the carrier retaining devices are rigidly attached to the translating member 23, some of the carrier retaining devices (e.g., the second carrier retaining device 27b and the fifth carrier retaining device 27e) are connected to the translating member 23 using attachment devices 28 that allow the cylindrical beams 32 to rotate about their center axes. Based on the requirements of the analysis system, some cylindrical beams 32 can rotate by different amounts than others. As shown, in some implementations, rotation is achieved by cam devices. In such implementations, each of the carrier retaining devices having rotating cylindrical beams include a pin 63 in the attachment device 28 that is mounted in an off-center position relative to the center axis of cylindrical beam 32 and moves along a slot 61 or 62 as the translating member 23 translates. As discussed in further detail below, based on the profile of the slots 61 or 62, different degrees of rotation can be achieved by forming slots that create different amounts of relative motion between the pin 63 and the cylindrical beam 32. In other implementations, rotation can be achieved by providing attachment devices with individual rotation mechanisms such as motors or actuators (e.g., electric motors, servos, or pneumatic actuators).

Figure 5:
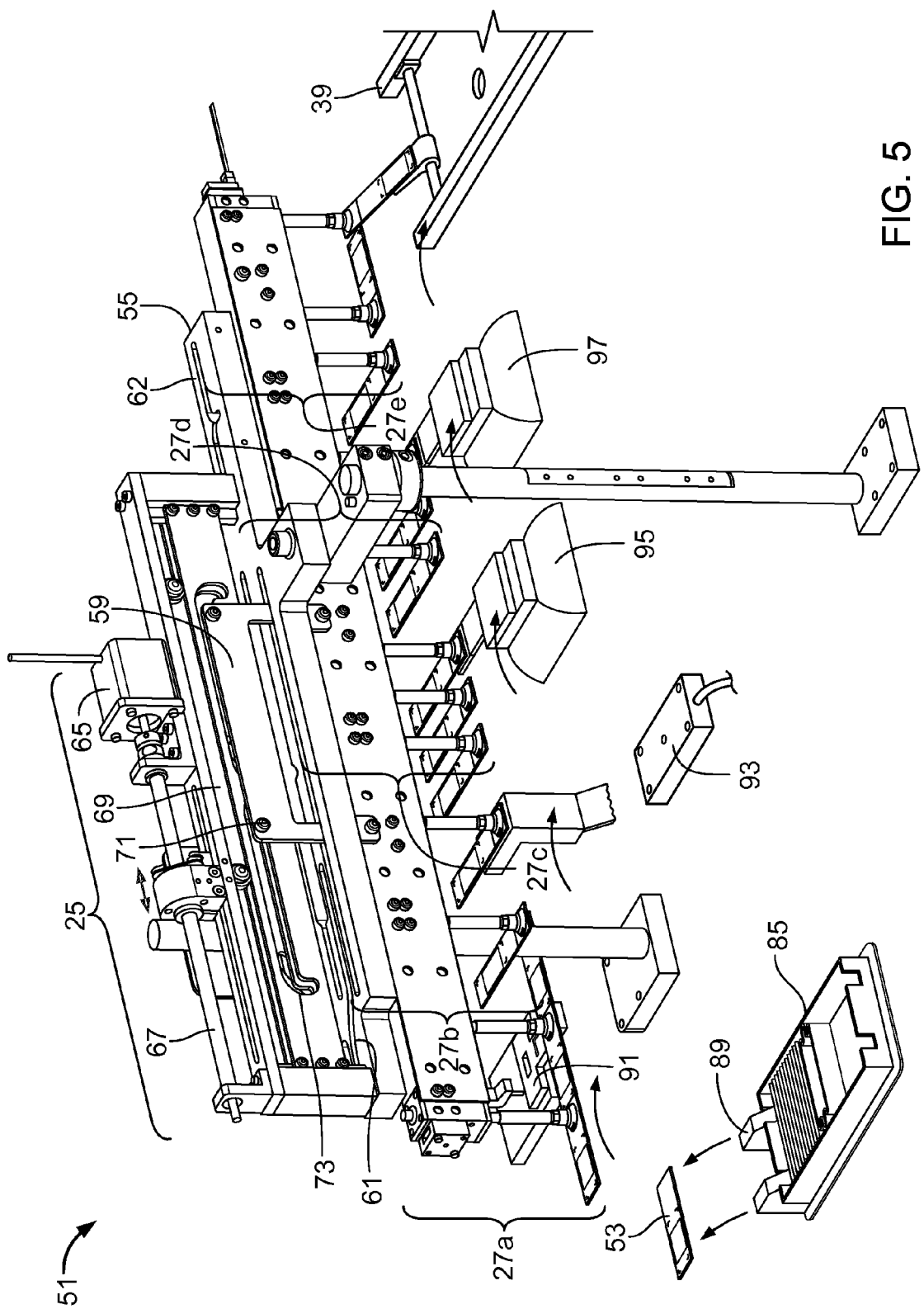
FIG. 5 is a perspective view of the slide transport system of FIG. 4A in operation, moving from a "pick-up" position through the home position of FIG. 4A to a "drop off" position.

FIG. 5 shows the motion of the components of the slide transport module 51 during operation as the slide transport module 51 translates from the pick-up position to the drop-off position. Thus, more cylindrical beams 32, vacuum cups 30, and glass slides 53 are shown, to simulate motion, than would actually be present in the system at any one time. As shown in this embodiment, the synchronous motion of carrier retaining devices 27 is controlled by the motion of the single electric motor 65 that is connected to the leadscrew 67. That is, the single electric motor 65 provides motive force for the vertical and horizontal movement of the sample carrier retaining devices, as well as the rotational movement of such carrier retaining devices. However, in other implementations, the desired synchronous motion can alternatively be achieved by more than one motor (e.g., separate motors, one to translate each of the one or more carrier retaining devices). As the electric motor 65 rotates, the leadscrew 67 drives the movement beam 69 which drives the connecting beam 59.

The connecting beam 59 then translates, following the path of the lift/lower slot 73 so that translating member 23 along with the carrier retaining devices are able to lower to contact glass slides 53 at processing stations. Once in contact at the pick-up position, the vacuum cups 30 apply vacuum to retain the glass slides 53, then the entire translating member 23 with carrier retaining devices 27a, 27b, 27c, 27d, and 27e with the glass slides 53 retained to the vacuum cups 30 lifts to remove the slides 53 from the processing stations, translates forward via the electric motor 65 and leadscrew 67, and then lowers to place the slides onto the next sequential processing station at the drop-off position. Once in contact with the next processing station, the vacuum cups 30 release vacuum and release the glass slides 53.

After the slides 53 are released, the translating member 23 and the carrier retaining devices 27a, 27b, 27c, 27d, and 27e with empty vacuum cups 30 lift, following the lift/lower slot 37, and translate backward. This movement and process can be repeated continuously to transport the glass slides 53 from processing station to processing station as the slide moves throughout the system, as discussed above with respect to FIG. 3.

Transportation of Slides

Figure 6:
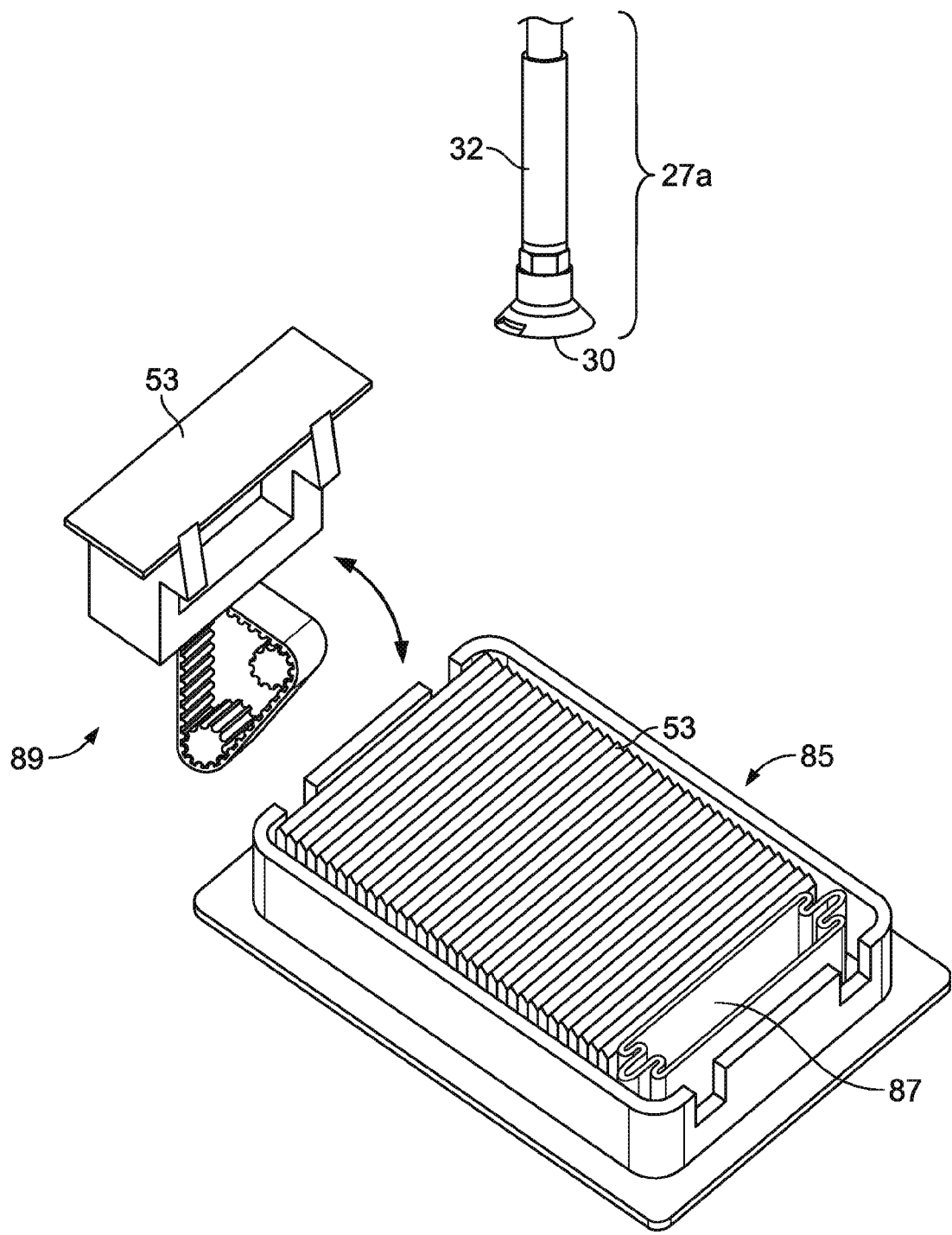
FIG. 6 is a perspective view of a slide magazine and feeder providing a slide to a slide input location of a slide transport system.

FIG. 6 shows a slide magazine 85 providing a slide 53 to a slide input location of the slide transport module 51. The slide magazine 85 contains multiple slides 53 arranged for removal and use in the fluid analysis system 31. In some implementations, the slide magazine 85 can have a deflecting device 87 (e.g., a spring) to push slides 53 towards an end of the magazine 85 where slides 53 are removed. Slides 53 are removed from the slide magazine 85 using a slide feeder 89 (e.g., utilizing a vacuum retaining force and two small fingers, one at each side of the slide). Once the slide 53 is removed from the slide magazine 85, the slide feeder 89 is rotated and/or translated upwards to provide the slide 53 to the slide input position to be picked up by a first carrier retaining device 27a.

Figure 14A:
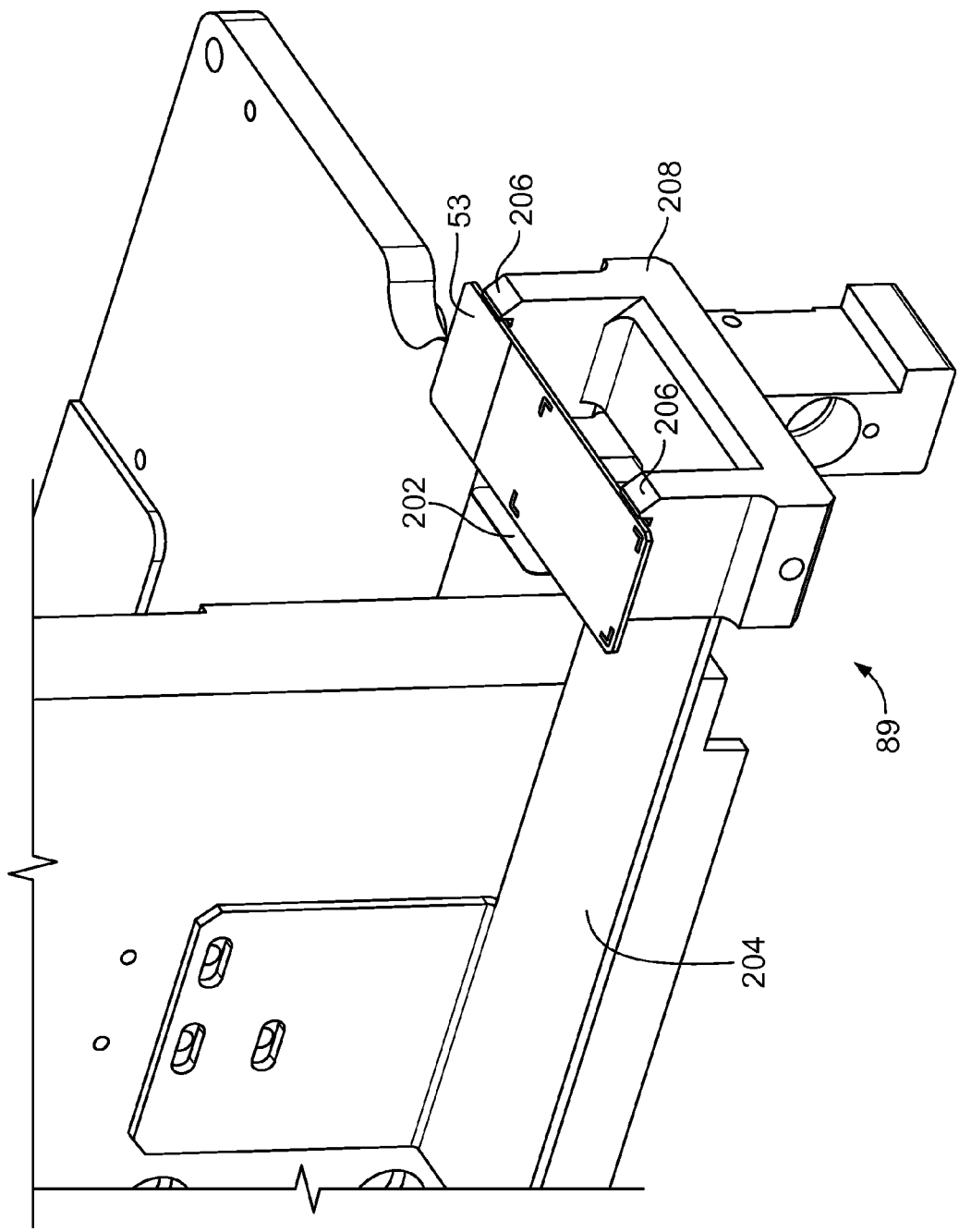
FIGS. 14A and 14B are perspective views of a slide feeder.
Figure 14B:
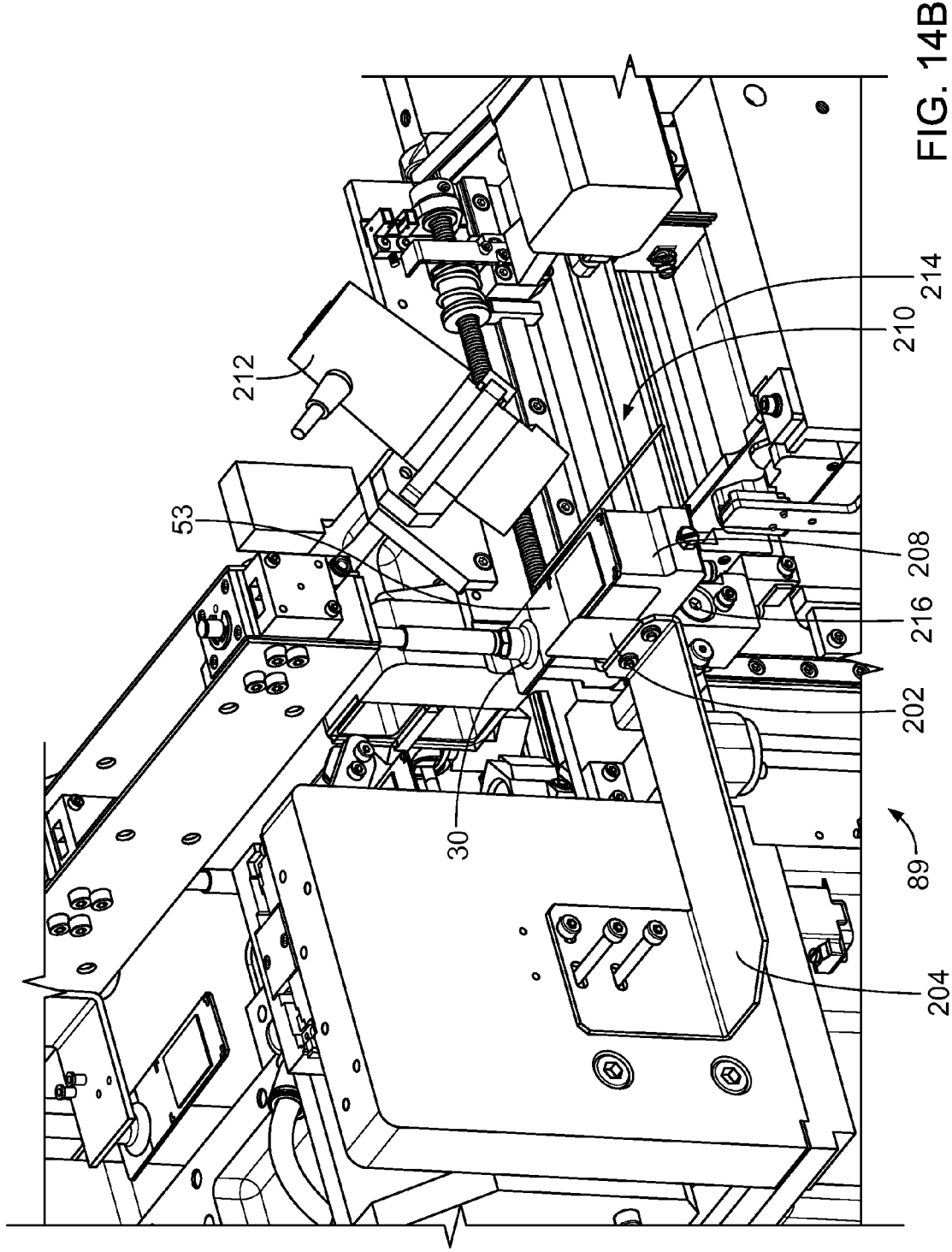

Another exemplary implementation of a slide feeder 89 is shown in FIGS. 14A and 14B. During operation of system 31, when sample carriers (e.g., microscope slides) are removed from a magazine by a slide feeder, it can be important to ensure that the carriers are reproducibly positioned at the same location on the slide feeder so that they can be reliably fed into system 31. If sample carriers are not reproducibly positioned, errors in sample dispensing and/or imaging can occur. To ensure accurate placement, slide feeder 89 shown in FIGS. 14A and 14B includes a mechanism for registering each slide 53 against tabs 206 after the slide is removed from magazine 214.

In FIGS. 14A and 14B, slide feeder 89 includes a gripper block 208 with tabs 206 at one edge of a slide support surface. Gripper block 208 rotates about a shaft 216, and includes one or more vacuum ports (not shown) extending to the slide support surface. Positioned in close proximity to gripper block 208 is a leaf spring 202 mounted to a support arm 204. During operation, gripper block 208 rotates about shaft 216 so that tabs 206 are positioned underneath a slide 53 in magazine 214. With a vacuum force applied to the slide support surface, a slide positioned on the slide support surface is withdrawn from magazine 214. Gripper block 208 rotates in the opposite direction about shaft 216, stopping with slide 53 in position 210 shown in FIG. 14B. A camera 212 obtains an image of slide 53, and the image is processed to ensure that slide 53 is genuine and catalogued.

Thereafter, gripper block 208 continues to rotate about shaft 216 until slide 53 is in the position shown in FIGS. 14A and 14B. When slide 53 is extracted from magazine 214, the vacuum force is applied to the slide support surface. As such, the primary retention force that maintains slide 53 in contact with the slide support surface is the vacuum force, not the force applied by tabs 206. Thus, slide 53 may not be perfectly registered against tabs 206 when it is first rotated into position as shown in FIGS. 14A and 14B.

To register slide 53 against tabs 206, the vacuum force applied to the slide support surface is discontinued. In its position on the slide support surface, slide 53 is contacted by leaf spring 202. Leaf spring 202 applies a force to the edge of slide 53 in the direction of tabs 206 (i.e., in a direction approximately parallel to the slide support surface), pushing slide 53 firmly against tabs 206. The vacuum force is then re-applied to the slide support surface, locking slide 53 in position against tabs 206. In this manner, reproducible positioning of slides on the slide support surface is achieved. After slide 53 has been positioned, suction cup 30 is lowered onto the edge of slide 53, the vacuum force on the slide support surface is released, and slide 53 is picked up by suction cup 30 and transported to another processing station.

Leaf spring 202 is typically formed from a compliant metal or alloy such as aluminum or stainless steel. In certain implementations, leaf spring 202 can be formed from an elastomeric material or a plastic material. Further, leaf spring 202 can be formed from a more rigid metal member, as long as care is taken to ensure that the force applied by leaf spring 202 does not damage slide 53.

In some implementations, leaf spring 202 can be replaced by another type of device for applying force to slide 53. For example, an air cylinder, a motorized aligner, or a motor-driven piston can be used to align slide 53 against tabs 206. In certain implementations, the vacuum force applied to the slide support surface can be discontinued before the slide support surface is horizontal, such that slide 53 is tilted in a position similar to position 210 when the vacuum force is removed. Slide 53 can slide downwards against the slide support surface under the influence of gravity until it contacts tabs 206, whereupon vacuum force can be re-established at the slide support surface to lock slide 53 into position. Thus, slide 53 can be registered against tabs 206 without using a leaf spring (or an equivalent mechanism).

Although leaf spring 202 is attached to support arm 204 in FIGS. 14A and 14B, in some implementations leaf spring 202 (or another similar mechanism) can be attached to a different component in system 31. In general, however, leaf spring 202 is not connected directly to gripper block 208. Further, as described above, gripper block 208 pauses its rotational movement to allow camera 212 to obtain an image of slide 53. In certain implementations, gripper block 208 rotates continuously between magazine 214 and the position shown in FIGS. 14A and 14B, and camera 212 obtains an image of slide 53 as the slide is actively being rotated by gripper block 208.

Figure 7:
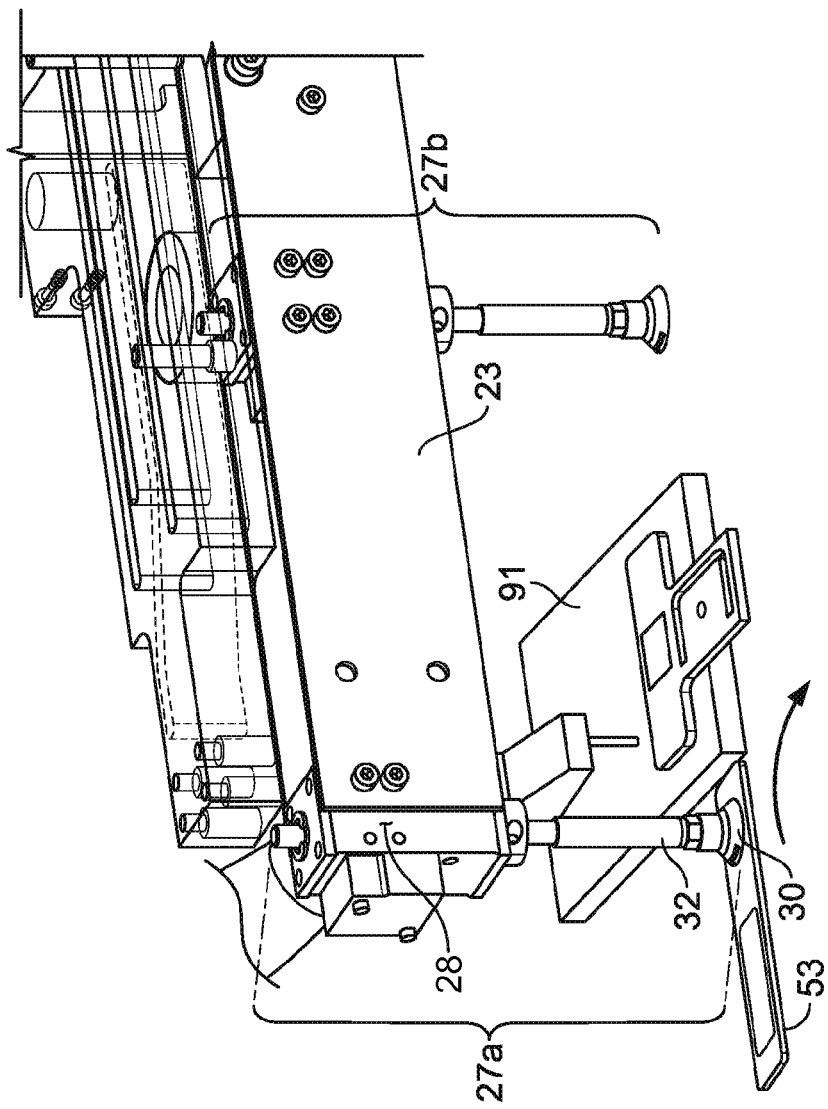
FIG. 7 is a perspective view of a slide being moved to a sample print station of FIG. 4A.
Figure 7:
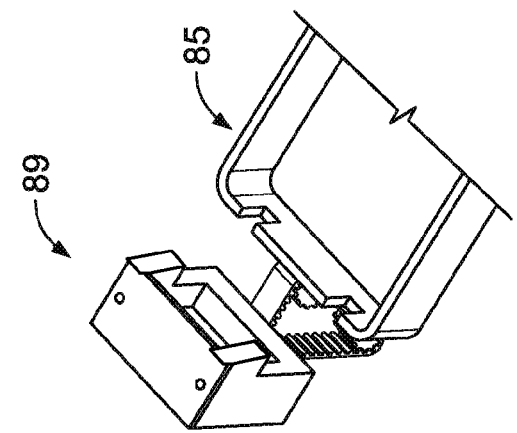

FIG. 7 shows a slide 53 being moved by the first carrier retaining device 27a, to a sample print station 91. To move the slide 53, the first carrier retaining device 27a is lowered to the pick-up position and the vacuum cup 30 is pressed on to contact the slide 53 at the input position. Once in contact, vacuum is applied to the vacuum cup 30 of the first carrier retaining device 27a so that when the first carrier retaining device 27a is lifted and translated by the translating member 23 as discussed above, the slide 53 is retained and transported. As slide 53 approaches the sample print station 91, the first carrier retaining device 27a lowers to place the slide 53 onto the sample print station 91. The vacuum is released from the vacuum cup 30 of first carrier retaining device 27a and the slide 53 is retained to the sample print station 91 by similar retention methods (e.g., vacuum). While the sample print station 91 applies a sample (e.g., a fluid sample) to the slide 53, the first carrier retaining device 27a translates back to the slide magazine feeder 89 and simultaneously a second carrier retaining device 27b translates from the next processing station (e.g., sample preparation station 93) towards the first processing station.

Figure 8:
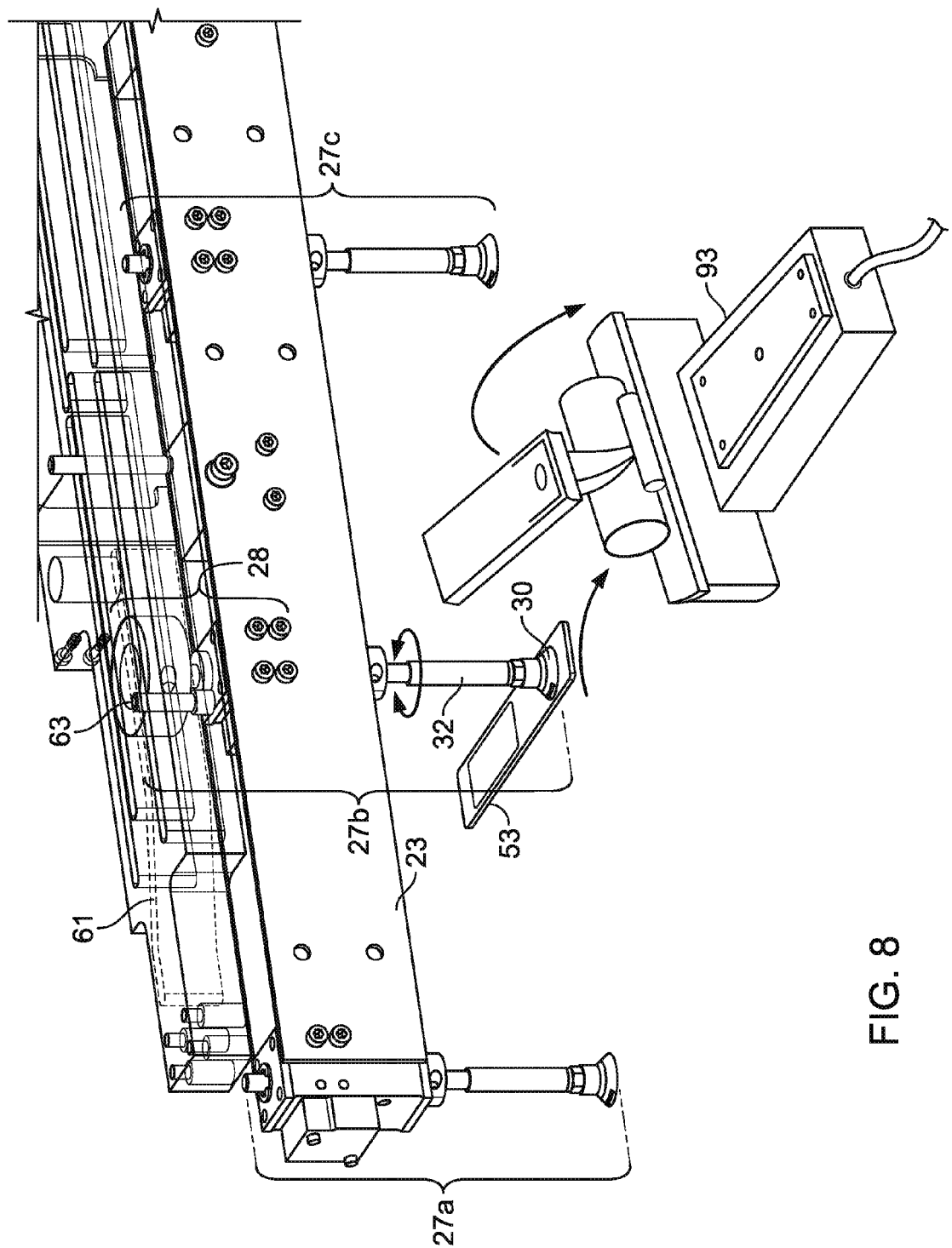
FIG. 8 is a perspective view of a slide being moved to a sample preparation station of FIG. 4A.

FIG. 8 shows a slide 53 being moved from the sample print station 91 to a sample preparation station 93. As discussed above, the second carrier retaining device 27b translates in unison with the first carrier retaining device 27a and travels towards the sample print station 91 and lowers to contact the slide 53. The vacuum applied from the sample print station 91 is released and vacuum is applied to the vacuum cup 30 of the second carrier retaining device 27b to retain the slide 53. Along with the translating member 23 and carrier retaining devices, the slide 53 is then lifted and translated forward. The second carrier retaining device 27b is attached to the translating member 23 such that the cylindrical beam 32 and vacuum cup 30 are free to rotate around the center axis of the cylindrical beam 32.

As shown, the attachment device 28 for the second carrier retaining device 27b has a pin 63 which moves along an angled slot 61 in the base beam 55. In some embodiments, one or more bearings can surround pin 63 and a sleeve can be placed over the bearings to decrease resistance as pin 63 travels along angled slot 61. The pin 63 is mounted at an off-center position relative to the center axis of cylindrical beam 32, and if the pin 63 is moved relative to the cylindrical beam 32 it can cause the cylindrical beam 32 to rotate. Therefore, when the pin 63 moves along the angled slot 61 during translation the angled slot 61 causes the pin 63 to move relative to the cylindrical beam 32. Therefore, the cylindrical beam 32 and vacuum cup 30 of the second carrier retaining device 27b rotate based on the position of the pin 63 within the slot's profile.

As shown, in this implementation, the profile of slot 61 is shaped so that the cylindrical beam 32 and vacuum cup 30 of the second carrier retaining device 27b will rotate 90° when the pin 63 translates along the angled slot to provide the slide 53 to the sample preparation station 93 in the proper orientation. As previously described, pin 63 can includes bearings and a sleeve or other rotary elements to reduce resistance and wear in the system as the pin travels back and forth along the angled slot.

The speed at which the second carrier retaining device 27b rotates while the pin 63 travels along the slot 61 depends on the transition and length of the angled portion, which influence the speed at which the pin 63 moves from one straight segment of the slot 61 to another straight segment of the slot 61. The faster the transition (i.e., the shorter the angled segment), the faster the pin 63 will move from one straight segment to another straight segment of the slot, and thus the faster the second carrier retaining device 27b moves as well. Therefore, the slot 61 profile can typically be optimized to control the rotational speed of the second carrier retaining device 27b based on system requirements (e.g., the longer distance over which the slot 61 causes rotation, the slower the rotation). Similar to the motion of the first carrier retaining device 27a, as the second carrier retaining device 27b approaches the sample preparation station 93, it lowers to place the slide 53 onto the and releases vacuum to the vacuum cup 30. While the second carrier retaining device 27b releases the slide 53 and translates backward toward the pick-up position, the sample preparation station 93 can apply one or more fixative, stain, and/or rinse solutions to the fluid sample. In some implementations, where sample preparation station 93 contains two or more locations for simultaneously preparing multiple samples, the sample preparation station can move horizontally with respect to the lowered position of carrier retaining device 27b to ensure that slide 53 is deposited in an available processing location of sample processing station 93.

Figure 9:
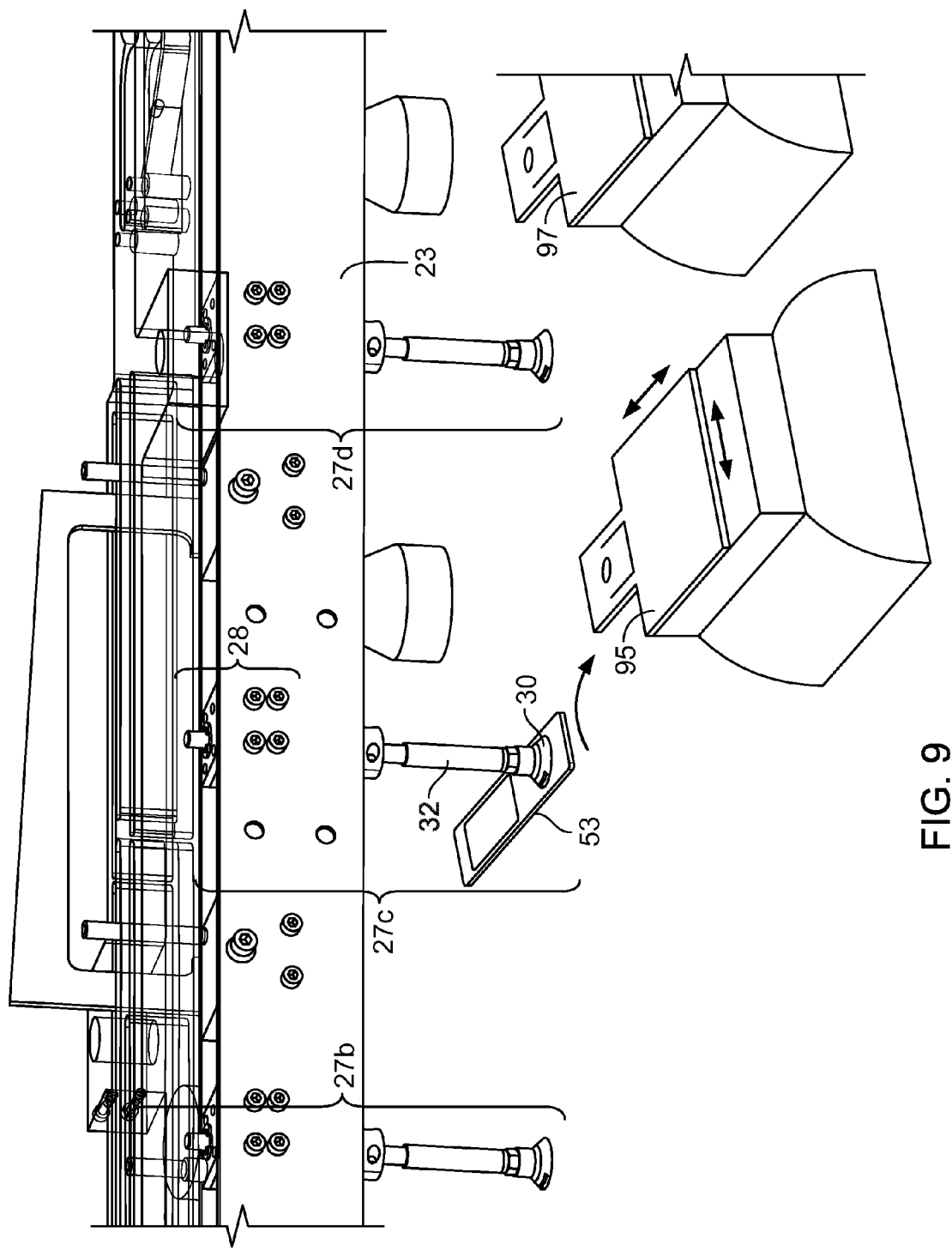
FIG. 9 is a perspective view of a slide being moved to a low magnification imaging station of FIG. 4A.

FIG. 9 shows a slide 53 being transported from the sample preparation station 93, e.g., a staining station, to a low magnification imaging station 95. Similarly to the previous carrier retaining devices, as the translating member 23 moves backward to the pick-up position, a third carrier retaining device 27c translates backward and a vacuum cup 30 is lowered to contact the slide 53 on the sample preparation station 93. Vacuum is applied to the vacuum cup of the third carrier retaining device 27c and the slide 53 is lifted from the sample preparation station 93 and translated toward the low magnification imaging station 95 as the translating member 23 moves forward toward the drop-off position. As the third carrier retaining device 27c and the slide 53 approach the low magnification imaging station 95, the slide 53 is lowered onto the low magnification imaging station 95.

Once the slide 53 is in contact with the low magnification imaging station 95, the third carrier retaining device 27c releases vacuum and the low magnification imaging station 95 retains the slide 53. As a low magnification image is taken of the sample on the slide 53, the translating member 23 translates backward toward the pick-up position.

As the low magnification image is taken of the sample, the translating member moves back to the pick-up position and a fourth carrier retaining device 27d translates backward toward the low magnification imaging station 95. As the fourth carrier retaining device 27d approaches the slide 53, the vacuum cup is lowered to contact the slide 53 and vacuum is applied to retain the slide 53. Via the motion of the translating member 23 toward the drop-off position, the slide 53 is then lifted from the low magnification imaging station 95 and translated forward towards a high magnification imaging station 97. As the fourth carrier retaining device 27d with the slide 53 approaches the high magnification imaging station 97, it is lowered to deliver the slide 53 to the high magnification imaging station 97. Once the slide 53 contacts the high magnification imaging station 97, the fourth carrier retaining device 27d releases the slide 53 and the high magnification imaging station 97 retains the slide 53. As the translating member 23 along with the fourth carrier retaining device 27d and vacuum cup 30 lifts to move backward toward the pick-up position, a high magnification image is taken of the fluid sample. As shown, in some implementations, the high magnification imaging station 97 is the final processing station, and once the high magnification image of the sample is taken, the slide 53 may be discarded or placed in storage for further consideration.

Figure 10:
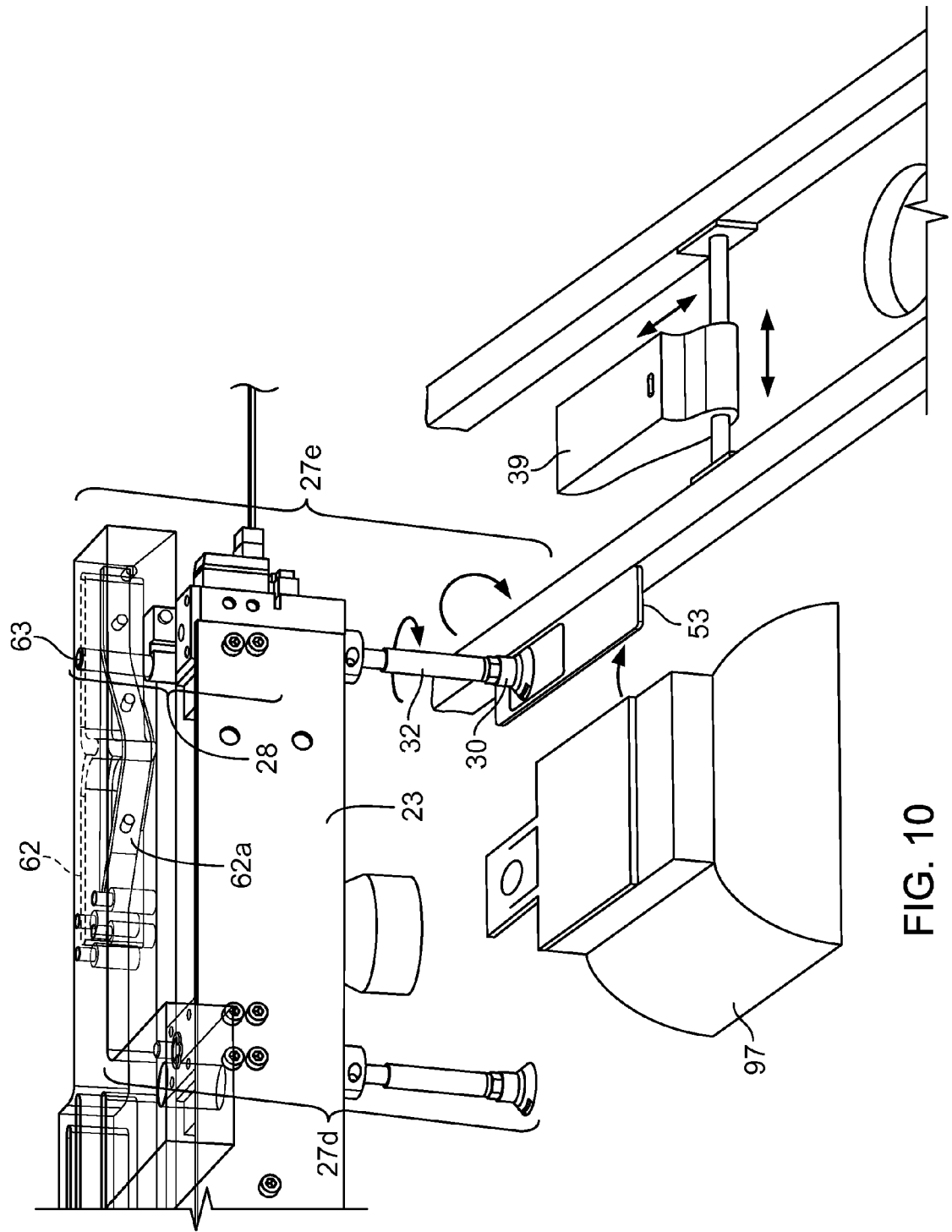
FIG. 10 is a perspective view of a slide being moved to a slide output station of FIG. 4A.

FIG. 10 shows a slide 53 being transported to a slide output station 39. Similar to the other carrier retaining devices, a fifth carrier retaining device 27e and vacuum cup 30 translates backward toward the high magnification imaging station 97, the vacuum cup 30 lowers to contact the slide 53, and applies vacuum to retain the slide 53. Then, along with the translating member 23, the fifth carrier retaining device 27e with vacuum cup 30 then lifts and translates forward toward the drop-off location to provide the slide 53 to the slide output station 39. Similar to the second carrier retaining device 27b, the attachment device for the fifth carrier retaining device 27e has a pin 63 that moves along a slot 62 to provide rotation to the cylindrical beam 32 and vacuum cup 30 of the fifth carrier retaining device 27e, and thus the retained slide 53. However, the slot 62 in which the pin 63 of the fifth carrier retaining device 27b moves is configured to rotate the cylindrical beam 32 and vacuum cup 30 of the fifth carrier retaining device 27e 180° about its center axis as it approaches the slide output station 39.

As shown in FIG. 10, the slot 62 includes two connected curved portions that, during translation of the translating member 23, cause the pin 63 to move with respect to cylindrical beam 32, and thus cause this beam, and the vacuum cup and attached slide, to rotate 180°. Slot 62 includes a spring member 62a that biases pin 63 toward the apex of the curved portion of slot 62 to ensure that pin 63 travels through slot 62 and cylindrical beam 32 completes the 180° rotation. Alternate profiles of slot 62 may be used in other implementations, with or without a spring member, and such alternate profiles can be configured to control the speed of rotation of cylindrical beam 32 as pin 63 travels through the slot. When the fifth carrier retaining device 27e is positioned at the pick-up position (i.e., picking up a slide from the high magnification imaging station), the pin 63 is positioned forward relative to a central axis of the cylindrical beam 32. As the pin moves through the first slot portion during translation, the motion of the pin 63 relative to the cylindrical beam 32 causes the beam to rotate 90° via the profile and shape of the slot. The slot is shaped such that as the translating beam 23 and fifth carrier retaining device 27e translate forward, the pin 63 momentarily stops moving forward and the cylindrical beam 32 passes the pin 63 relative to the forward direction. Then, as the pin 63 follows the second curved portion of the slot, the motion of the pin 63 relative to the cylindrical beam 32 rotates the cylindrical beam 32 an additional 90°. This method of rotation works in the same way as the fifth carrier retaining device 27e translates backward. As the fifth carrier retaining device 27e approaches the slide output station 39, it lowers to place the slide 53 in contact with the slide output station 39, the fifth carrier retaining device 27e releases vacuum, and the slide output station 39 retains the slide.

Figure 11:
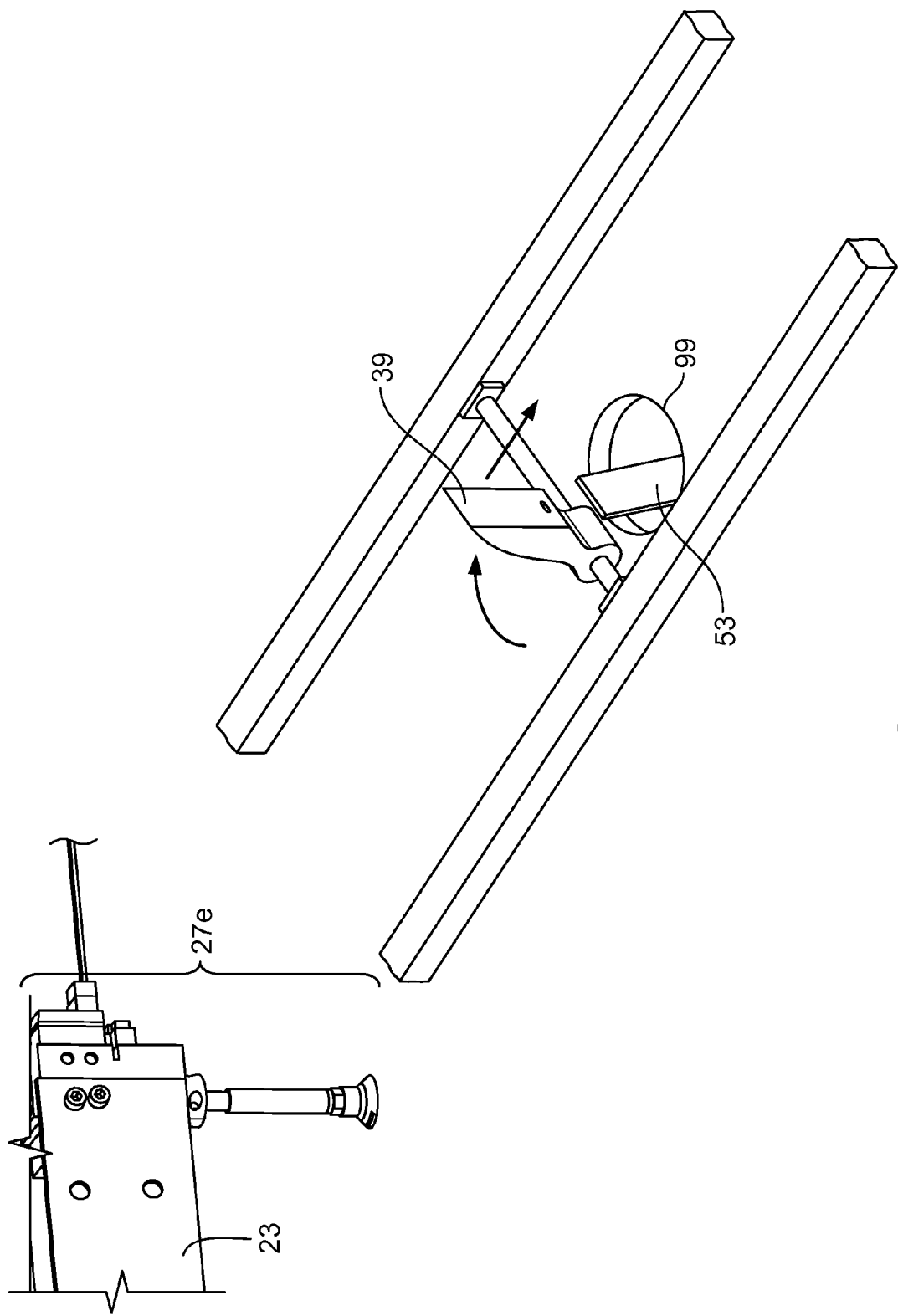
FIG. 11 is a perspective view of the slide output station of FIG. 4A discarding a slide.

FIG. 11 shows the slide output station 39 discarding the slide 53. In some cases, the analysis system 31 determines that the sample/slide does not need to be saved for further processing. As shown, in such cases, the slide 53 is discarded by releasing the slide 53 down a waste opening 99 to a waste receptacle.

Figure 12:
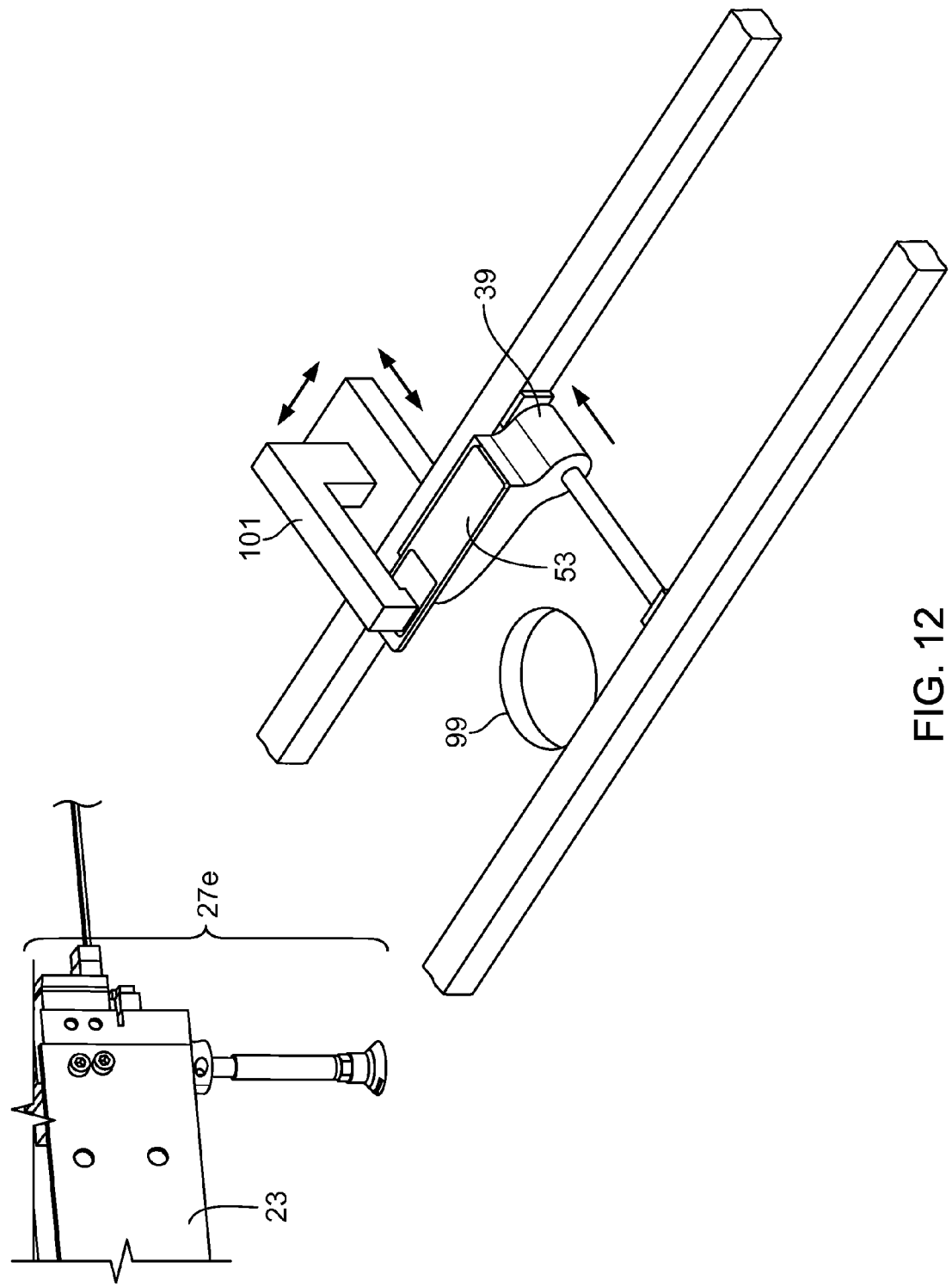
FIG. 12 is a perspective view of the slide output station of FIG. 4A transporting a slide to a printer station.

FIG. 12 shows the slide output station 39 of FIG. 11 transporting a slide 53 to a printer station 101. In some cases, instead of discarding the slide, the analysis system 31 determines, or is otherwise directed to keep the slide 53 and/or fluid sample from a patient for further inspection and/or processing. In such cases, the patient's information and/or the sample information (e.g., patient name, sample identification information) is generally applied to the slide for identification purposes. Therefore the slide 53 is translated to a printer station 101 where a printer prints patient information (e.g., in the form of a barcode that is readable by a computer device) onto the slide 53 for future inspection.

Figure 13:
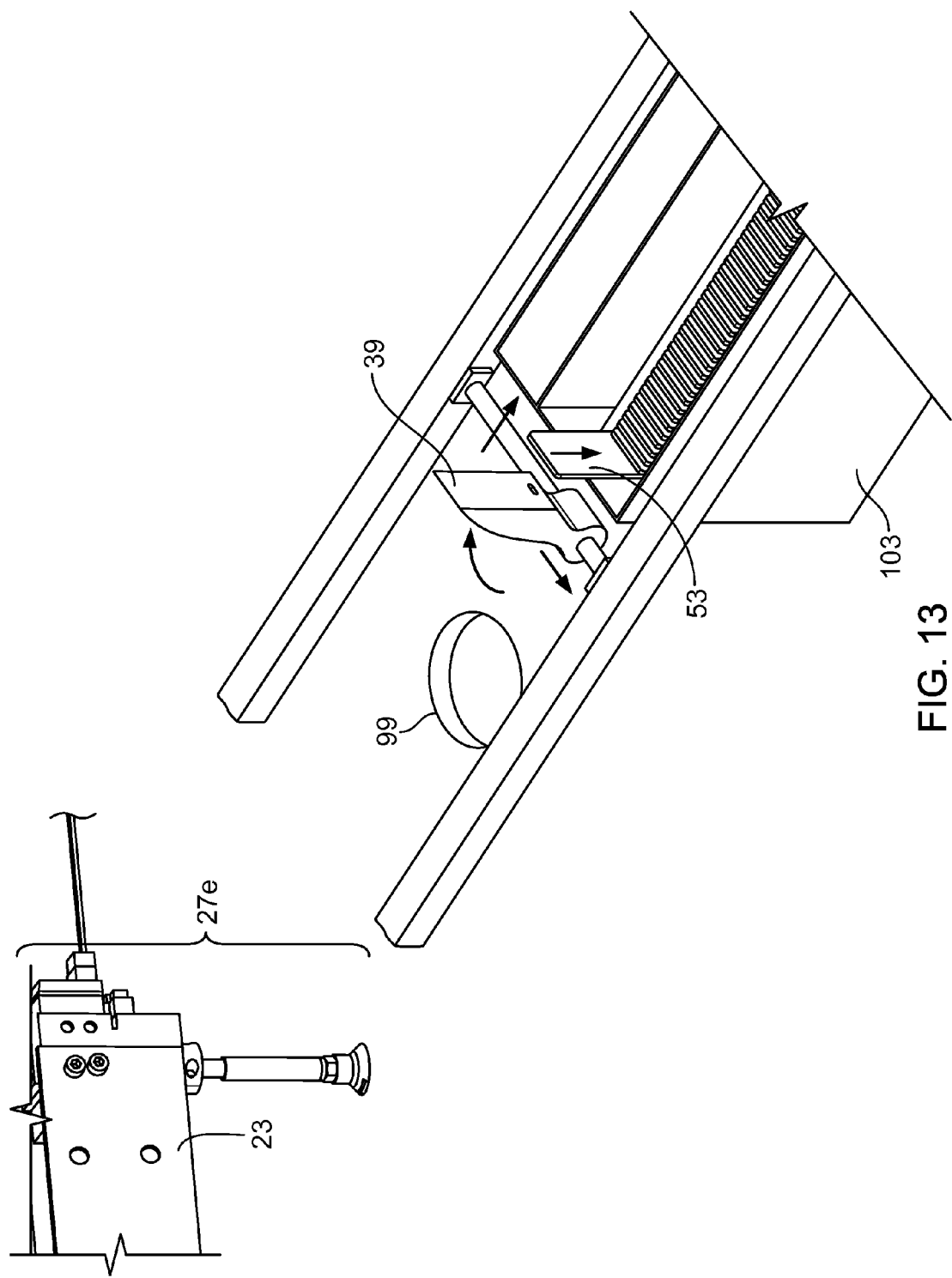
FIG. 13 is a perspective view of the slide output station of FIG. 4A transporting a slide to a slide storage magazine.

FIG. 13 shows the slide output station 39 of FIG. 11 transporting a slide 53 to a slide storage magazine 103. In some cases, when the slide 53 is retained, as discussed above, the slide 53 with patient information can be provided to and stored in a slide storage magazine 103. In such cases the slide 53 is translated to the slide storage magazine 103 and released into the output magazine 103. Slides 53 can be added to the slide storage magazine 103 until the slide storage magazine 103 is full of slides 53, then the slide storage magazine 103 can be removed from the system and an empty slide storage magazine can be provided.

Other Embodiments

It is to be understood that the foregoing description is intended to illustrate and not limit the scope of the disclosure, which is defined by the scope of the appended claims. Other aspects, advantages, and modifications are within the scope of the following claims.

What is claimed is:

1. A sample transport system that moves a sample carrier from one station to a next station in a sample processing system, the sample transport system comprising:
    a translating member;
    two or more sample carrier retaining devices attached to the translating member at a fixed, equal spacing between adjacent sample carrier retaining devices, wherein each of the two or more sample carrier retaining devices comprises a retainer portion to temporarily retain one or more sample carriers; and
    a movement mechanism connected to the translating member to move the translating member and the attached sample carrier retaining devices back and forth between a first position and a second position,
    wherein the sample carrier retaining devices are all moved and controlled simultaneously to enable each respective retainer portion to contact and retain a sample carrier when the translating member reaches the first position and to release a sample carrier when the translating member reaches the second position, such that as the translating member moves back and forth between the first position and the second position, sample carriers are advanced successively from one station to a next station in the sample processing system; and
    wherein the movement mechanism moves all sample carrier retaining devices vertically and horizontally between a first position and a second position and rotates a subset of the sample carrier retaining devices so that one or more sample carriers are positioned in a proper orientation at the second position.

2. The system of claim 1, wherein the movement mechanism comprises an electric motor and leadscrew.

3. The system of claim 1, wherein the movement mechanism comprises pneumatic or magnetic linear actuator.

4. The system of claim 1, wherein the retainer portions comprise a vacuum cup, an adhesive material, an electromagnet, or a mechanical device configured to hold a sample carrier.

5. The system of claim 1, wherein the movement mechanism rotates each member of the subset of the sample carrier retaining devices about an axis that extends through the member.

6. The system of claim 1, wherein the sample carrier comprises one or more of a metal, glass, ceramic, or plastic.

7. The system of claim 6, wherein the sample carrier is a glass slide.

8. The system of claim 1, wherein the sample processing system comprises six stations and the sample transport system comprises five sample carrier retaining devices.

9. The system of claim 8, wherein the sample processing system comprises:
    a slide magazine to provide empty sample carriers;
    a sample applicator configured to apply an aliquot of a sample to sample carriers;
    a sample stainer configured to apply one or more stains to samples on sample carriers;
    a low magnification imaging station to image at least a portion of samples on sample carriers;
    a high magnification imaging station to image a portion of samples on sample carriers; and
    a slide output station,
    wherein the sample transport system comprises five sample carrier retaining devices that successively advance sample carriers from one station to a next station in the sample processing system.

10. The system of claim 1, further comprising a device to lift and lower the translating member to simultaneously lift and lower all attached sample carrier retaining devices.

11. The system of claim 10, wherein the device to lift and lower the translating member comprises a member that travels along a profiled aperture within a horizontal beam.

12. The system of claim 1, wherein at least one of the sample carrier retaining devices is moved and controlled by the translating member to transport the sample carrier to a specific station in a proper orientation to retain or release the sample carrier at the specific station.

13. The system of claim 12, wherein the proper orientation of the sample carrier is achieved by rotating at least the retainer portion as the sample carrier retaining device moves towards the specific station.

14. The system of claim 13, wherein the proper orientation of the sample carrier is achieved by rotating at least the sample retainer portion horizontally to a specific angle from 90 to 180 degrees.

15. A method of transporting a sample on a sample carrier from one station to a next station in a sample processing system, the method comprising:
  obtaining a translating member that moves back and forth between a first position and a second position, wherein two or more sample carrier retaining devices are attached to the translating member at a fixed, equal spacing between adjacent sample carrier retaining devices;
  using a movement mechanism to move the translating member into the first position such that the sample carrier retaining devices are all moved and controlled simultaneously to contact and retain a sample carrier at a station; and
  using the movement mechanism to move the translating member into the second position such that the sample carrier retaining devices are all moved and controlled simultaneously to release a sample carrier at a station,
  wherein sample carriers are advanced successively from one station to a next station in the sample processing system; and
  wherein using the movement mechanism to move the translating member into the first and second positions moves all sample carrier retaining devices vertically and horizontally between a first position and a second position and rotates a subset of the sample carrier retaining devices so that one or more sample carriers are positioned in a proper orientation at the second position.

16. The method of claim 15, wherein moving the translating member between the first position and the second position comprises using an electric motor and a leadscrew of the movement mechanism to move the translating member.

17. The method of claim 15, wherein moving the translating member between the first position and the second position comprises using a pneumatic or magnetic linear actuator of the movement mechanism to move the translating member.

18. The method of claim 15, wherein moving the translating member comprises raising the translating member to remove a sample carrier from a station and lowering the translating member to place a sample carrier onto the next successive station.

19. The method of claim 15, wherein the sample carrier retaining devices each include a retainer portion comprising a vacuum cup, an adhesive material, an electromagnet, or a mechanical device configured to hold a sample carrier.

20. The method of claim 15, further comprising moving at least one of the two or more sample carrier retaining devices from a last successive station to a sample output mechanism.

21. The method of claim 15, wherein using the movement mechanism to move the translating member into the first and second positions rotates each member of the subset of the sample carrier retaining devices about an axis that extends through the member.

22. The method of claim 15, wherein each sample carrier is provided to the next successive station in a proper orientation associated with the next successive station.

23. The method of claim 15, wherein the sample comprises a body fluid.

24. The method of claim 23, wherein the body fluid is blood.

25. A sample transport system that moves a sample carrier from one station to a next station in a sample processing system, the sample transport system comprising:
  a translating member;
  two or more sample carrier retaining devices attached to the translating member at a fixed, equal spacing between adjacent sample carrier retaining devices, wherein each of the two or more sample carrier retaining devices comprises a retainer portion to temporarily retain a different sample carrier by contacting the sample carrier only on a surface of the sample carrier on which a sample is deposited; and
  a movement mechanism connected to the translating member and configured to:
    move the translating member and the attached sample carrier retaining devices back and forth horizontally and vertically between a first position and a second position; and
    rotate a subset of the sample carrier retaining devices so that one or more sample carriers are positioned in a proper orientation at the second position.

* * * * *